United States Patent
Manri et al.

(10) Patent No.: US 9,562,917 B2
(45) Date of Patent: Feb. 7, 2017

(54) AUTOMATIC ANALYSIS DEVICE AND AUTOMATIC ANALYSIS PROGRAM

(75) Inventors: Chihiro Manri, Tokyo (JP); Satoshi Mitsuyama, Tokyo (JP); Tomonori Mimura, Tokyo (JP); Kumiko Kamihara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 705 days.

(21) Appl. No.: 14/117,717

(22) PCT Filed: Apr. 17, 2012

(86) PCT No.: PCT/JP2012/060348
§ 371 (c)(1),
(2), (4) Date: Dec. 19, 2013

(87) PCT Pub. No.: WO2012/157386
PCT Pub. Date: Nov. 22, 2012

(65) Prior Publication Data
US 2014/0136123 A1    May 15, 2014

(30) Foreign Application Priority Data
May 16, 2011   (JP) .................................. 2011-109558

(51) Int. Cl.
*G01N 31/00*  (2006.01)
*G01N 35/00*  (2006.01)
*G01N 35/04*  (2006.01)

(52) U.S. Cl.
CPC .. *G01N 35/00584* (2013.01); *G01N 35/00693* (2013.01); *G01N 2035/00673* (2013.01);
(Continued)

(58) Field of Classification Search
CPC ............... G01N 2035/00673; G01N 35/00693; G01N 2035/00702; G01N 2035/0453; G01N 35/00584; G01N 35/00663; G01N 35/00623; G01N 2035/0097
(Continued)

(56) References Cited

U.S. PATENT DOCUMENTS 6,549,661 B1 *  4/2003  Mitsuyama ........ G06K 9/00127
356/39
7,785,534 B2 *  8/2010  Watari ............... G01N 35/1002
422/63

(Continued)

FOREIGN PATENT DOCUMENTS

JP    60-161560 A    8/1985
JP    04-191958 A    7/1992
(Continued)

OTHER PUBLICATIONS

Chinese Office Action received in corresponding Chinese Application No. 201280023897.9 dated Jul. 2, 2014.
(Continued)

*Primary Examiner* — An Do
(74) *Attorney, Agent, or Firm* — Mattingly & Malur, PC

(57) ABSTRACT

Accuracy control of an automatic analysis device that mixes a sample and a reagent to measure temporal change of a mixed solution is realized. A plurality of measurement point data is acquired from a reaction process of the sample and the reagent. Parameters and test values of approximate equations for approximating the plurality of measurement point data are accumulated in a storage unit. A distribution map of reference data corresponding to the parameters or the test values is created based on predetermined numbers of the parameters or the test values accumulated in the storage unit. Next, a plurality of screens for individually superimposing, on the distribution map, curved lines corresponding to a plurality of regression function candidates obtained by (Continued)

applying a plurality of regression functions are arranged and presented on a display screen, so as to approximate the data to the distribution map of the reference data.

11 Claims, 28 Drawing Sheets

(52) U.S. Cl.
CPC ............. *G01N 2035/00702* (2013.01); *G01N 2035/0453* (2013.01)

(58) Field of Classification Search
USPC ............... 702/19, 22, 27, 30; 422/63–65, 67
See application file for complete search history.

(56) References Cited

U.S. PATENT DOCUMENTS

| | | | |
|---|---|---|---|
| 9,476,893 B2* | 10/2016 | Mitsuyama | G01N 35/00623 |
| 9,494,525 B2* | 11/2016 | Tarumi | G01N 21/82 |
| 2011/0021368 A1 | 1/2011 | Tammero et al. | |
| 2011/0082648 A1 | 4/2011 | Matsumoto | |
| 2012/0064636 A1 | 3/2012 | Mitsuyama et al. | |
| 2012/0109534 A1 | 5/2012 | Kamihara et al. | |

FOREIGN PATENT DOCUMENTS

| | | | |
|---|---|---|---|
| JP | 04-286940 A | 10/1992 |
| JP | 2000-181903 A | 6/2000 |
| JP | 2004-317431 A | 11/2004 |
| JP | 2006-023214 A | 1/2006 |
| JP | 2006-300613 A | 11/2006 |
| JP | 2010/261822 A | 11/2010 |
| JP | 2010-271095 A | 12/2010 |
| JP | 2011-075493 A | 11/2014 |
| WO | 2010099170 A1 | 9/2010 |
| WO | 2010/134277 A1 | 11/2010 |
| WO | 2010128575 A1 | 11/2010 |

OTHER PUBLICATIONS

Extended European Search Report received in corresponding European Application No. 12785094.9 dated Mar. 20, 2015.

* cited by examiner

| Test item | Reagent code | Approximate equation |
|---|---|---|
| Item A | Reagent a | Expression 2 |
| Item A | Reagent b | Expression 3 |
| Item B | Reagent c | Expression 5 |
| Item B | Reagent d | Expression 8 |
| : | : | : |

| Test item | Reagent code | Evaluation parameter | | |
|---|---|---|---|---|
| | | A0 | TI | ... |
| Item A | Reagent a | ○ | × | ... |
| Item A | Reagent b | × | × | ... |
| Item B | Reagent c | × | × | ... |
| Item B | Reagent d | × | ○ | ... |
| : | : | : | : | : |

Fig. 9

| Test item | Reagent code | Vertical axis | Horizontal axis |
|---|---|---|---|
| Item A | Reagent a | A0 | A1 |
| Item A | Reagent a | Err | A1 |
| Item A | Reagent b | Err | A1 |
| Item B | Reagent d | A1 | Test value |
| : | : | : | : |

Fig. 13

| Test item | Reagent code | Approximate equation/evaluation parameters and test values used to create reference data | Threshold for selecting removal data |
|---|---|---|---|
| Item A | Reagent a | A0 | +2SD |
| | | A1 | ±2SD |
| Item B | Reagent b | Test value | ±1SD |
| : | : | : | : |

Fig. 22A

| Sample ID 2301 | Test item 2302 | Reference data ID 2303 | Approximate equation/evaluation parameters 2304 | Removal determination result 2305 | Deviation determination result 2306 | Reason of removal 2307 | Reason of deviation 2308 |
|---|---|---|---|---|---|---|---|
| ID1 | Item A | A_××OO△△ | (A1$_1$, Err$_1$) | Remove | — | Stirring abnormal | — |
| ID2 | Item A | A_××OO△△ | (A1$_2$, Err$_1$) | — | Deviated | — | Discontinuous measurement values |
| ID2 | Item B | B_××OO□□ | (A1$_2$, A0$_2$) | — | Normal | — | — |
| .. | .. | .. | .. | .. | .. | .. | .. |

2300

AUTOMATIC ANALYSIS DEVICE AND AUTOMATIC ANALYSIS PROGRAM

TECHNICAL FIELD

The present invention relates to an automatic analysis device for qualitative or quantitative analysis of a sample and to a program for realizing the processing function. For example, the present invention relates to an automatic analysis device having a function of monitoring reaction in clinical test analysis and to a program for realizing the processing function.

BACKGROUND ART

In an automatic analysis device for clinical test, certain amounts of sample and reagent are dispensed to induce reaction, and the absorbance of a reaction solution is measured for a certain time to obtain test values (concentrations or activity values) of a measurement target substance based on a measurement result. The test result plays an important role in various diagnoses by a doctor, such as figuring out medical conditions of a patient and determining effects of therapy. Therefore, accuracy control for ensuring correct measurement by the automatic analysis device is essential.

An example of a general accuracy management method includes a method of measuring an accuracy control sample with a known concentration and comparing the measurement result with a predetermined tolerance. The measurement and the comparison of the accuracy control sample are periodically executed between measurements of general (patient) specimens. If the measurement result of the accuracy control sample is within the tolerance, it can be determined that the measurement of the general specimens executed between the previous measurement of the accuracy control sample and the measurement this time is correctly executed.

An example of a method of ensuring the accuracy of the measurement of individual general specimens includes an accuracy management method using reaction process data (reaction process curve) (for example, see Patent Literature 1 and 2). The reaction process data denotes time-series data of the absorbance measured for a plurality of times after reaction of a reagent with a sample. The measurement method of clinical test is roughly divided into two types, an end-point method and a rate method, and the reaction process curve varies according to the methods.

The end-point method is used to measure concentrations of components, such as protein and fat mainly included in the sample. A substance generated by reaction of a component in the sample with a reagent becomes asymptotic to a certain amount with time, and the measurement value also becomes asymptotic to a certain value with time.

The rate method is mainly used to measure activities of enzyme components included in the sample, and instead of the concentration of an enzyme, an activity value of the enzyme is measured. A reagent and a certain amount of substrate are added to the sample to measure the activity value, and elements changed by consumption of the substrate by the enzyme are measured based on the reagent. The enzyme reaction rate is theoretically asymptotic to the upper limit if the substrate concentration is high on some level. A reagent for biochemical item measurement includes a sufficient amount of substrate. Therefore, if the reaction of the sample with the reagent is normal, the measurement value of the reaction in general linearly changes by certain amounts relative to the time change.

Patent Literature 1 and 2 illustrates methods of using an approximate equation derived based on a chemical reaction model to approximate a reaction process curve and comparing obtained approximate equation parameters and the like with a predetermined standard distribution of parameters (distribution of normal parameters or distribution of normal parameters and abnormal parameters). In the methods, if the approximate equation parameters and the like are included in a normal range, it is determined that the measurement is performed correctly. Patent Literature 1 describes an accuracy management method related to the end-point method, and Patent Literature 2 describes an accuracy management method related to the rate method.

CITATION LIST

Patent Literature

Patent Literature 1: JP Patent Publication (Kokai) No. 2010-261822 A
Patent Literature 2: JP Patent Publication (Kokai) No. 2010-271095 A

SUMMARY OF INVENTION

Technical Problem

However, the accuracy management method using the accuracy control sample cannot determine the stage of an occurrence of abnormality after the measurement using the accuracy control sample of the last time, even if an abnormal value is detected in the measurement result of the latest accuracy control sample. Therefore, there is a problem that the measurement accuracy cannot be ensured for all general specimens measured meantime. Although there is a method of increasing the measurement frequency of the accuracy control sample to solve the problem, the accuracy control sample and the reagent are generally expensive. Therefore, the method of increasing the measurement frequency has another problem that the burden of expenses of the user increases.

Patent Literature 1 and 2 describes a method of individually determining abnormality of reaction process data of a general specimen.

However, even if the test items are the same, the shapes of the reaction process curves may not be the same if the reagent used for the measurement is different (for example, if the manufacturer, home-made, or the lot is different). Therefore, the distribution of the standard parameters needs to be created again every time the reagent manufacturer, the lot, or the like is changed.

Furthermore, abnormal data is caused by various factors, such as an abnormality derived from a patient, an abnormality derived from a device, and an abnormality derived from a reagent, and the frequency of appearance of the abnormal data is significantly low. Therefore, long-term accumulation of data is necessary to set the distribution of the standard parameters. However, as described above, the distribution of the standard parameters changes when the reagent lot or the like is changed. More specifically, it is generally difficult to create the distribution of the standard parameters in a period in which the distribution shape does not change. Therefore, the accuracy control based on the methods illustrated in Patent Literature 1 and 2 still has limitations in the accuracy.

Solution to Problem

Therefore, an invention proposes an automatic analysis device that mixes a sample and a reagent to measure temporal change of a mixed solution, the automatic analysis device including: (a) a measurement point data acquisition unit that acquires a plurality of measurement point data from a reaction process of the sample and the reagent; (b) a first storage unit that accumulates test values and parameters of approximate equations for approximating the plurality of measurement point data; (c) a data processing unit that creates a distribution map of reference data corresponding to the parameters or the test values based on predetermined numbers of the parameters or the test values accumulated in the first storage unit; (d) a second storage unit that stores a plurality of regression functions; and (e) an output unit that arranges and presents, on a display screen, a plurality of screens for individually superimposing, on the distribution map, curved lines corresponding to a plurality of regression function candidates obtained by applying the plurality of regression functions, so as to approximate the distribution map of the reference data.

An invention presents an automatic analysis device that mixes a sample and a reagent to measure temporal change of a mixed solution, the automatic analysis device including: (a) a measurement point data acquisition unit that acquires a plurality of measurement point data from a reaction process of the sample and the reagent; (b) a first storage unit that accumulates test values and parameters of approximate equations for approximating the plurality of measurement point data; (c) a data processing unit that creates a distribution map of reference data corresponding to the parameters or the test values based on predetermined numbers of the parameters or the test values accumulated in the first storage unit; (d) a second storage unit that stores a threshold for removal determination; (e) an output unit that presents, on a display screen, removal data candidates included in the distribution map of the reference data based on the threshold; and (f) a third storage unit that stores attached information of the reference data, the information including a determination result indicating whether data is to be removed from the distribution map of the reference data.

Advantageous Effects of Invention

According to the present invention, even if the reagent lot or the like is changed, the user can create a distribution of reference data used as a determination standard, based on objective information. As a result, the accuracy of the accuracy control of individual reagents can be improved.

Other problems, configurations, and advantageous effects will become apparent from the following description of embodiments.

BRIEF DESCRIPTION OF DRAWINGS

FIG. 9 is a diagram showing an example of a table describing a relationship between test items, types of reagent, and approximate equation/evaluation parameters as well as test values used for deviation determination.

FIG. 13 is a diagram showing an example of a table describing a relationship between test items, types of reagent, approximate equation/evaluation parameters as well as test values used to create reference data, and thresholds for selecting removal data.

FIG. 22A is a diagram showing a table configuration for storing removal determination results.

DESCRIPTION OF EMBODIMENTS

Hereinafter, embodiments of the present invention will be described with reference to the drawings. The content of device configurations and processing operation described later is an example for describing the invention. The present invention also includes inventions derived by combining already-known techniques with the device configurations and the processing operation described later and includes inventions derived by replacing part of the device configurations and the processing operation described later by already-known techniques.

The embodiments described below are roughly divided into the following three processing functions.
(1) Creation of a distribution map of reference data and removal of abnormal data.
(2) Deviation determination for the distribution map of reference data and presentation of a deviation determination result.
(3) Creation of a distribution map that can identify normal data/abnormal data.

One of the processing functions relates to a creation process of reference data used for deviation determination and the like. As described in the problems, the distribution map of reference data needs to be created again at a timing of a change in the reagent manufacturer, the lot, or the like. Alternatively, the reference data may be created again in each period designated by the user, such as every week or every month. The distribution map of reference data may be created again for every certain number of test data designated by the user, such as when 1000 test data are accumulated. When the distribution map of reference data is changed, an applied regression function is also generally changed.

One of the processing functions relates to a process of presenting the user with a result of deviation determination performed by a device (program) using the distribution map of reference data. The user can check the test data determined to be deviated from a normal range, at the end of a day or at a timing before the test result is reported to the doctor or the like. This can improve the accuracy of the accuracy control.

One of the processing functions relates to a process of creating a distribution map of normal data/abnormal data. After the distribution map of reference data is created again along with a change in the reagent lot or the like, a distribution map that allows continuously identifying normal data and abnormal data can be created to improve the accuracy of long-term accuracy control

[First Embodiment]
[Device Configuration]

Figure 2:
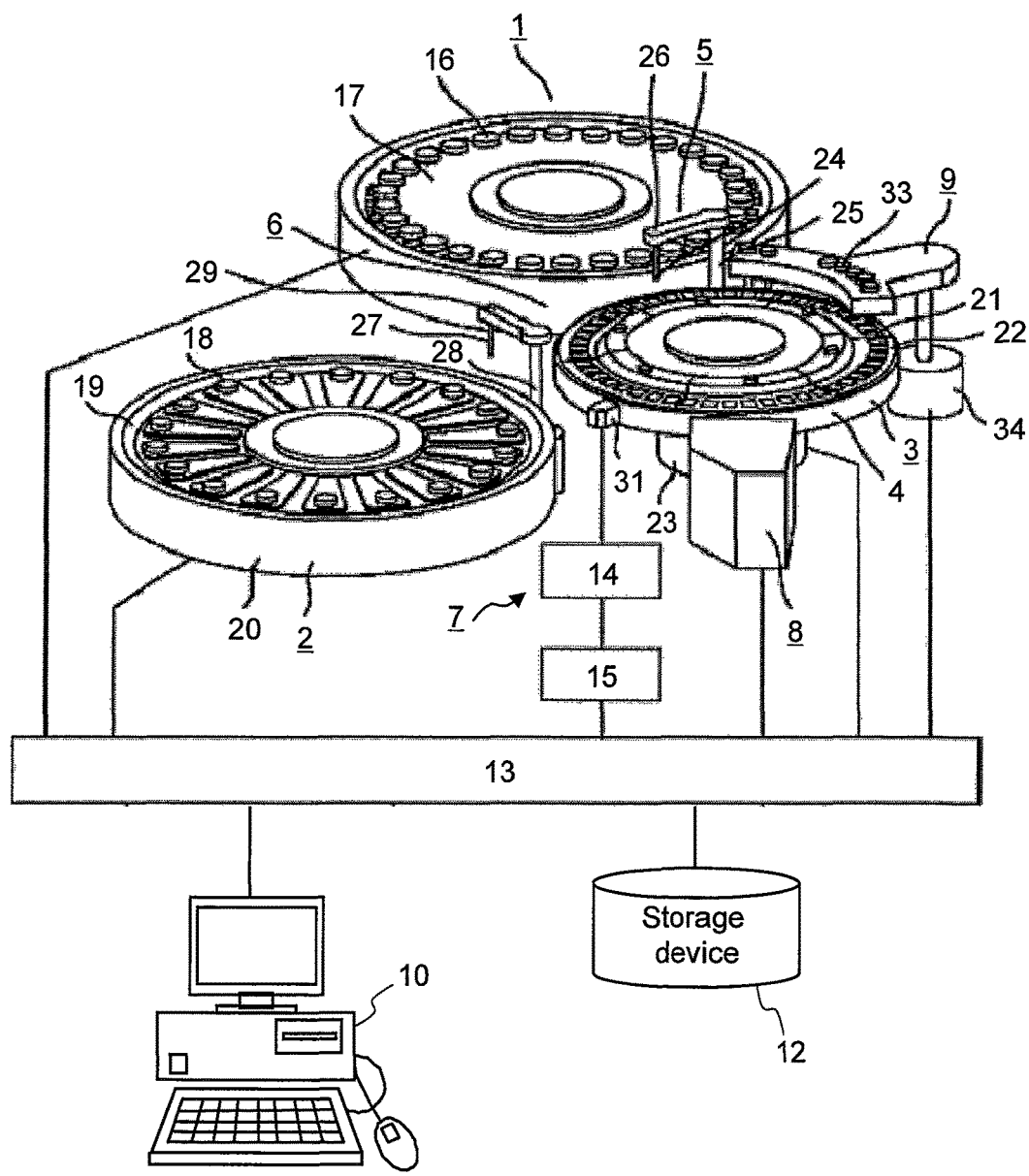
FIG. 2 is a diagram describing a schematic configuration of an automatic analysis device.

Hereinafter, a device configuration and processing operation of an automatic analysis device according to a first embodiment will be described in detail with reference to the drawings. FIG. 2 shows an example of a schematic configuration of a biochemical automatic analysis device with the analysis functions described above.

The biochemical automatic analysis device includes a sample disk 1, a reagent disk 2, a reaction disk 3, a reaction tank 4, a specimen sampling mechanism 5, a pipetting mechanism 6, a stirring mechanism 7, a photometric mechanism 8, a cleaning mechanism 9, a computer (PC) 10, a storage device 12, a control unit 13, a piezoelectric element driver 14, a stirring mechanism controller 15, sample containers 16, circular disks 17 and 19, a reagent container 18, a cooling box 20, a reaction vessel 21, a reaction vessel holder 22, a drive mechanism 23, a sampling probe 24, bearing shafts 25 and 28, arms 26 and 29, a reagent dispensing probe 27, a fixation portion 31, a nozzle 33, and a vertical drive mechanism 34.

The storage device 12 stores analysis parameters, the number of times each reagent bottle can perform analysis, the maximum number of times each reagent bottle can perform analysis, calibration results, analysis results, and the like.

The analysis of a sample in the biochemical automatic analysis device is performed in the order of sampling, reagent dispensing, stirring, photometry, cleaning of reaction vessel, and data processing such as concentration conversion.

The control unit 13 controls the sample disk 1 through the computer 10. A plurality of sample containers 16 are arranged and installed on the circumference of the sample disk 1. The sample containers 16 are moved below the sampling probe 24 according to the order of analysis. A sample pump connected to the specimen sampling mechanism 5 dispenses predetermined amounts of specimens in the sample containers 16 into the reaction vessel 21.

The reaction vessel 21 provided with the samples is moved inside of the reaction tank 4, up to an adding position of a first reagent. A reagent pump (not shown) connected to the reagent dispensing probe 27 adds a predetermined amount of the reagent sucked from the reagent container 18 to the moved reaction vessel 21. After the first reagent is added, the reaction vessel 21 is moved to the position of the stirring mechanism 7, and first stirring is performed. The addition and the stirring of the reagent are performed for first to fourth reagents, for example.

The reaction vessel 21 with the stirred content is arranged in a luminous flux emitted from a light source. Part of the luminous flux passes through the reaction vessel 21, and part of the luminous flux is absorbed by the content. The photometric mechanism 8 formed by, for example, a multi-wavelength photometer detects the degree of absorption. The photometric mechanism 8 outputs, to the control unit 13, measurement point data (absorbance signal) including the degrees of absorption regarding the specimens detected along with the passage of time.

Through the data processing described later, the control unit 13 performs creation of reference data, determination of removal data, determination of deviation data, creation of normal/abnormal pattern, and the like. The reference data, the removal data, the deviation data, and the like created by the control unit 13 are all stored in the storage device 12 and displayed on a display device belonging to the computer 10. The reaction vessel 21 finished with the photometry is transferred to the position of the cleaning mechanism 9 and is used for the next analysis after cleaning.

Figure 4:
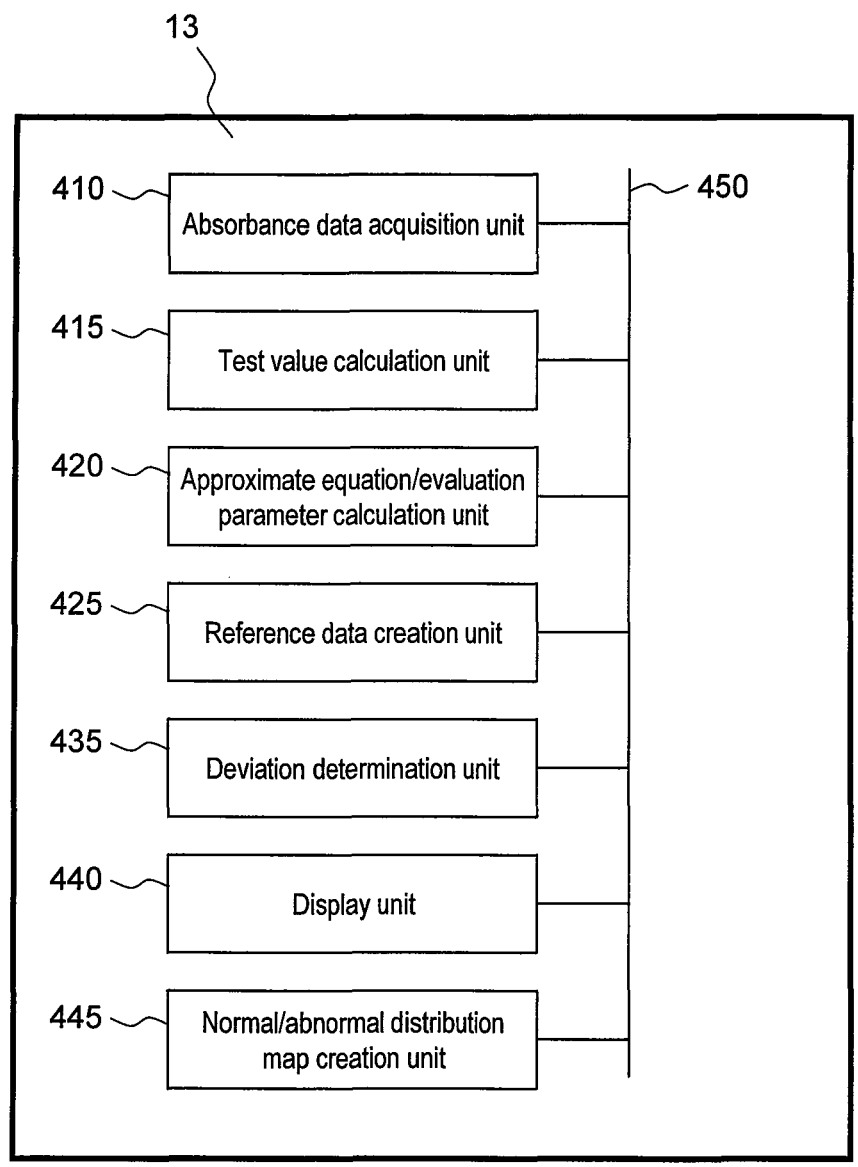
FIG. 4 is a diagram showing an example of an internal configuration of a control unit.

FIG. 4 shows an example of an internal configuration of the control unit 13 that realizes the processing function. FIG. 4 illustrates a program realizing the processing function, from the viewpoint of hardware. The control unit 13 shown in FIG. 4 includes an absorbance data acquisition unit 410, a test value calculation unit 415, an approximate equation/evaluation parameter calculation unit 420, a reference data creation unit 425, a deviation determination unit 435, a display unit 440, a normal/abnormal distribution map creation unit 445, and a data bus 450 for mutually connecting these.

The components shown in FIG. 4 can mutually transfer data through the data bus 450. The functional blocks included in the control unit 13 may be hardware or a CPU other than the control unit 13. Obviously, the functional blocks included in the control unit 13 may be software modules mounted on the same CPU.

[Processing Operation]
(1) A creation processing procedure of reference data and (2) a deviation determination processing procedure and a check processing procedure of a deviation determination result executed by the control unit 13 will be described in the present embodiment.

Figure 1:
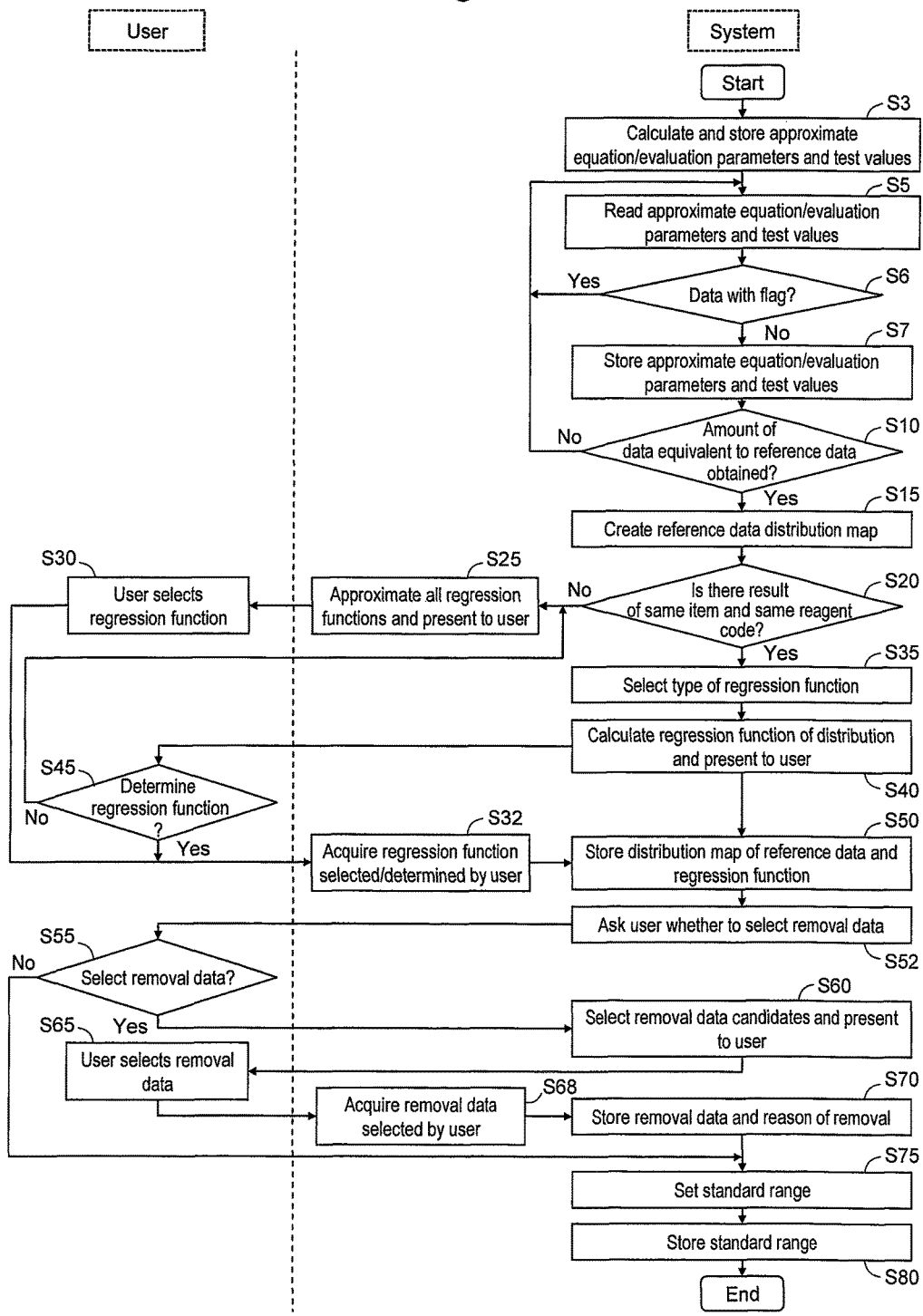
FIG. 1 is a flow chart describing a processing procedure according to a first embodiment.

FIG. 1 shows the creation processing procedure of reference data (including a determination processing procedure of removal data).

[Creation Process of Reference Data (FIG. 1)]
[Step S3]

The control unit 13 calculates and records approximate equation parameters, evaluation parameters, and test values. The absorbance data acquisition unit 410, the test value calculation unit 415, and the like are used in this process.

Figure 3:
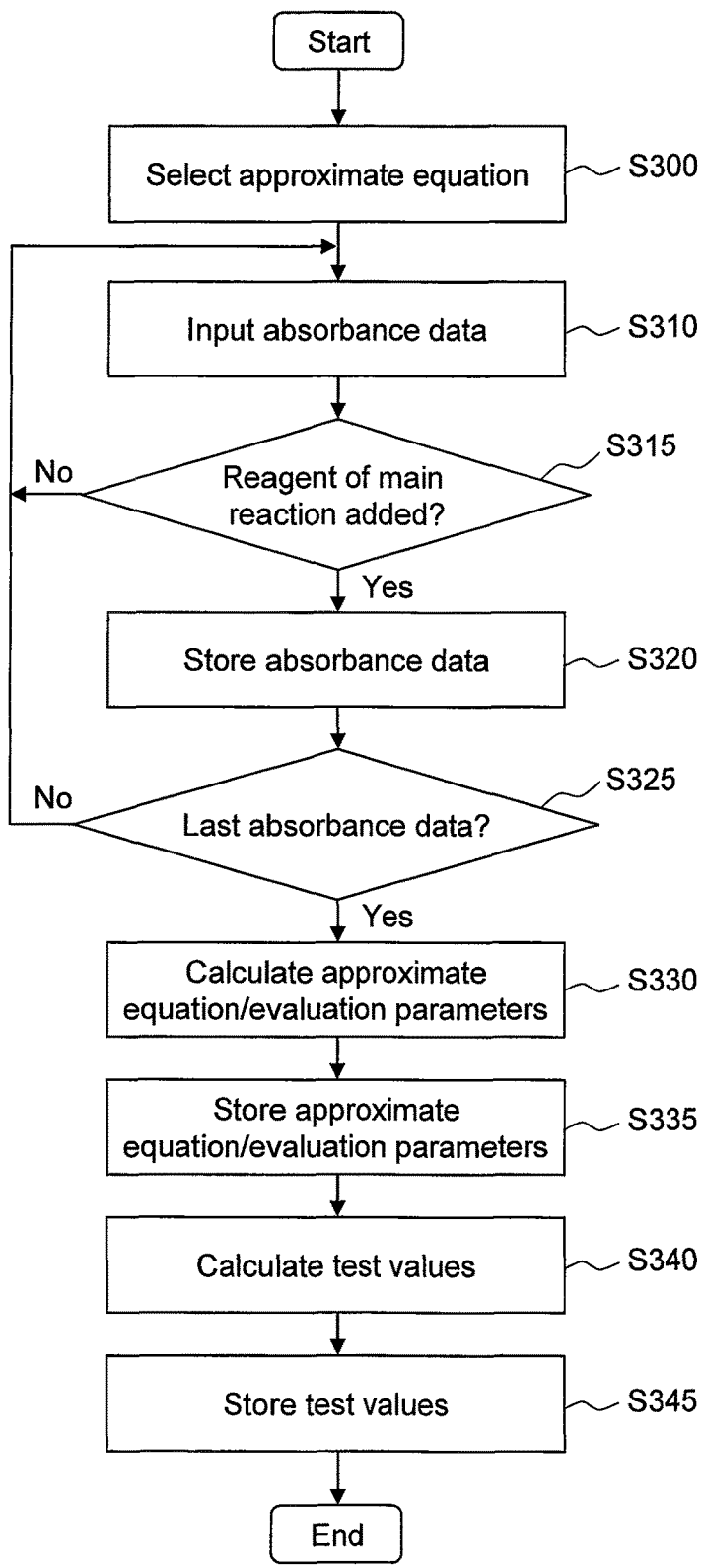
FIG. 3 is a flow chart describing a calculation procedure of parameters and test values.

FIG. 3 shows a detailed procedure of the process. When the measurement of a test item is started, the approximate equation/evaluation parameter calculation unit 420 selects and reads an optimal approximate equation corresponding to the combination of the test item and the reagent code in step S300. A plurality of approximation equations as selection targets indicating the time change of the absorbance are stored in advance in the storage device 12. Examples of selectable approximate equations in the present embodiment include functions indicated by Expressions 1 to 8.

$$x = a*t + b + c*\exp(-k*t) \quad \text{(Expression 1)}$$

$$x = a*t + b + e/(t+d) \quad \text{(Expression 2)}$$

$$x = a*t + b + w/\{\exp(u*t) + v\} \quad \text{(Expression 3)}$$

$$x = a*t + b + p*\log\{1 + q*\exp(r*t)\} \quad \text{(Expression 4)}$$

$$x = a0 - a1*\exp(-k*t) \quad \text{(Expression 5)}$$

$$x = a0 - a1*\exp(-k1*t) - a2*\exp(-k2*t) \quad \text{(Expression 6)}$$

$$x = a + k/(t+b) \quad \text{(Expression 7)}$$

$$x = a + b/(\exp(k*t) + c) \quad \text{(Expression 8)}$$

In the functions, t denotes time, and x denotes absorbance. The characters a, b, c, d, e, k, p, q, r, u, v, w, a0, a1, k1, and k2 are approximate equation parameters.

The functions indicated in Expressions 1 to 4 are mainly applied to the rate method, and the functions indicated in Expressions 5 to 8 are mainly applied to the end-point method. Obviously, the functions are not limited to these, and other functions can also be prepared as approximate equations.

The approximate equation/evaluation parameter calculation unit 420 automatically selects the approximate equation based on the combination of the test item and the reagent code. To realize the function, a table associating a most suitable approximate equation with each combination of the test item and the reagent code is used, for example. The table can be stored in the storage device 12, for example. The approximate equation/evaluation parameter calculation unit 420 searches the table based on the combination of the test item and the reagent code and selects the optimal approximate equation corresponding to the combination.

Figures 5, 6:
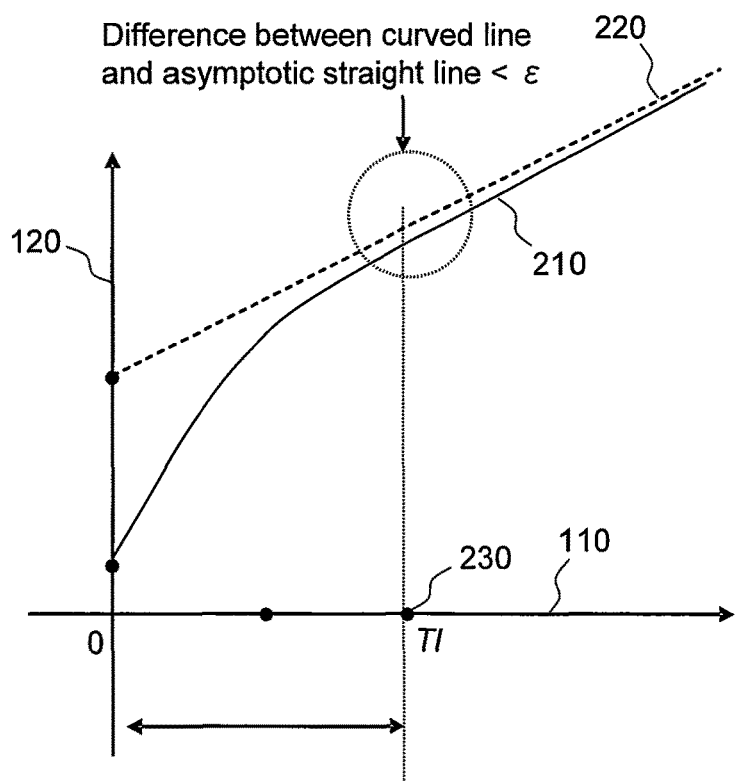
FIG. 5 is a diagram showing an example of a table describing a relationship between test items, types of reagent, and optimal approximate equations.
FIG. 6 is a diagram describing evaluation parameters.

FIG. 5 shows an example of the table. A table 500 includes columns 510, 520, and 530. Test items are described in the column 510. Reagent codes indicating the types of reagents are described in the column 520. Optimal approximate equations associated with the test items and the types of the reagent codes are described in the column 530.

In this embodiment, the approximate equation/evaluation parameter calculation unit 420 searches the table 500 based on the combination of the test item and the reagent code and selects an optimal approximate equation corresponding to the combination of the test item and the reagent code. The user may be able to change the content of the correspondence stored in the table 500.

The absorbance is measured for a plurality of times along with the passage of time. In the following step S310, the absorbance data acquisition unit 410 receives absorbance data of one measurement or an average of a plurality of measurements from the photometric mechanism 8. More specifically, the absorbance data is input to the control unit 13. In a measurement system using light at a wavelength (main wavelength) with a large change in the absorbance in response to a color change associated with the reaction of the reagent with the specimen and using light at a wavelength (sub-wavelength) with almost no change in the absorbance, a difference between the absorbance of the main wavelength light and the absorbance of the sub-wavelength light is input as the absorbance data.

In step S315, the absorbance data acquisition unit 410 determines whether a main reaction reagent is added. If it is determined that the main reaction reagent is not added, the processing process returns to step S310, and the next absorbance data is input. The determination operation is repeatedly executed until it is determined that the main reaction reagent is added. The main reaction reagent denotes a reagent (usually, the final reagent) that causes a main absorbance change in the reaction using a plurality of reagents. If the main reaction reagent is added, the processing process moves to step S320.

In step S320, the absorbance data acquisition unit 410 stores the input absorbance data in the storage device 12.

In step S325, the absorbance data acquisition unit 410 determines whether the last absorbance data is stored. If it is determined that the last absorbance data is not stored in the storage device 12, the processing process returns to step S310. This loop operation (input and storage of absorbance data) is repeatedly executed until a necessary number of data is stored in the storage device 12. If the absorbance data acquisition unit 410 determines that the necessary number of data is accumulated, the processing process proceeds to step S330.

In step S330, the approximate equation/evaluation parameter calculation unit 420 calculates values of the parameters in the expression to reduce, as much as possible, the difference between the time change of the absorbance expressed by the approximate equation selected in step S300 and the actual time change of the absorbance. Specifically, the parameter values in the expression are calculated to reduce, as much as possible, a square error between the absorbance data stored as a measurement result and the absorbance data at the corresponding time calculated by the approximate equation. An existing least-squares calculation method can be used to calculate the parameter values. An example of a method that can handle expressions in various forms includes a method of using a steepest descent method to calculate the parameter values that minimize the square error.

In step S330, the approximate equation/evaluation parameter calculation unit 420 calculates evaluation parameters. Examples of the evaluation parameters include an average value of differences (errors) between the absorbance (approximate values) calculated by the approximate equations and the absorbance (actual measurement values) in the actual measurement, a mean square value of errors, and a maximum value of errors.

As shown for example in the following Expression 9, approximate equation parameters indicated in Expressions 1 to 8 can be combined to perform various calculations, and the obtained values can be used.

$$A0 = a0 - a1 \quad \text{(Expression 9)}$$

Expression 9 is an example of an expression for using the approximate equation parameters indicated in Expression 5 to obtain evaluation parameter values indicating the initial absorbance ("A0") of the end-point method. Parameters indicating the shape of a reaction process curve may also be used, for example.

FIG. 6 is a diagram describing equation parameters indicating the shape of a reaction process curve of the rate method. In FIG. 6, a horizontal axis 110 denotes the elapsed time from the start of reaction, and a vertical axis 120 denotes the absorbance. A curved line 210 denotes an approximate curve line of absorbance change obtained by the approximate equations. A straight line 220 is a straight line to which the curved line 210 is asymptotic. A point 230 on the horizontal axis 110 denotes time T1 at which the curved line 210 is sufficiently asymptotic to the straight line 220, and a range of 0 to T1 of the horizontal axis 110 is equivalent to a lag time section. In this case, T1 can be used as the evaluation parameter.

The lag time section denotes a curved section that may appear before the reaction rate becomes constant (straight line) due to factors, such as concentration of specimen, condition of stirring, and reaction temperature, in the rate method. A small value $\epsilon$ is set in advance, and the sufficiently asymptotic time is defined as time at which the difference between the curved line 210 and the straight line 220 becomes equal to or smaller than $\epsilon$, for example. The value $\epsilon$ may be a certain value or may be set according to the initial absorbance or the amount of change in the absorbance. For example, a value obtained by multiplying the initial absorbance by a constant or a value obtained by multiplying a difference between the initial absorbance and the final absorbance by a constant may be set as $\epsilon$.

A small value $\delta$ may be set in advance, and the sufficiently asymptotic time may be defined as time at which the difference between slopes of the curved line 210 and the straight line 220 becomes equal to or smaller than $\delta$. In this case, $\delta$ may be a certain value or may be set according to the slope of the straight line 220. For example, a value obtained by multiplying the slope of the straight line 220 by a constant may be set as $\delta$.

The evaluation parameters and the calculation method are stored in advance in the storage device 12. The approximate equation/evaluation parameter calculation unit 420 automatically selects the evaluation parameters based on the combination of the test item and the reagent code. To realize the function, a table including the correspondence between the combinations of the test items and the reagent codes and the evaluation parameters can be stored in the storage device 12, for example. The approximate equation/evaluation parameter calculation unit 420 searches the table based on the combinations of the test items and the reagent codes to select combinations of the evaluation parameters corresponding to the combinations.

Figures 7, 8:
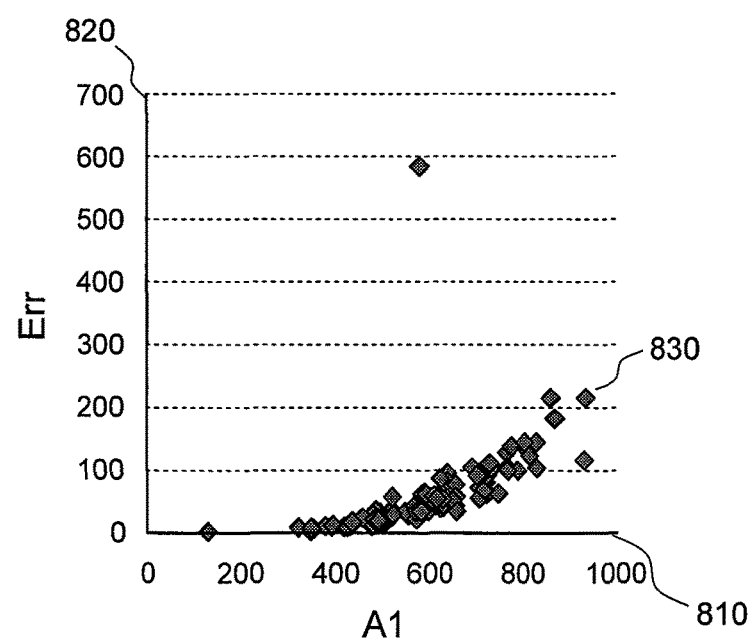
FIG. 7 is a diagram showing an example of a table describing a relationship between test items, types of reagent, and evaluation parameters.
FIG. 8 is a diagram describing an example of a distribution map of reference data.

FIG. 7 shows an example of the table. A table 700 includes columns 710, 720, and 730. The test items are described in the column 710. The types of reagents are described in the column 720. The combinations of the evaluation parameters associated with the test items and the types of reagent codes are described in the column 730. In FIG. 7, a symbol "O" denotes that the parameter is adopted, and a symbol "X" indicates that the parameter is not adopted. The evaluation parameter may not be selected, or one or a plurality of evaluation parameters may be combined and selected. All of the evaluation parameters may be selected. In this embodiment, the approximate equation/evaluation parameter calculation unit 420 searches the table 700 based on the combination of the test item and the reagent code and selects the combination of the evaluation parameters associated with the combination of the test item and the reagent code. The user may be able to change the content of the correspondence stored in the table 700.

In step S335, the approximate equation/evaluation parameter calculation unit 420 stores approximate equation parameter values and evaluation parameter values in the storage device 12, for each combination of the test item and the reagent code.

In step S340, the test value calculation unit 415 calculates test values from the obtained absorbance data based on a calibration curve. The calibration curve data is stored in advance in the storage device 12.

In step S345, the test value calculation unit 415 stores the test values calculated for each combination of the test item and the reagent code in the storage device 12.

[Step S5]

FIG. 1 will be described again. In step S5, the reference data creation unit 425 searches the storage device 12 based on the combination of the designated test item and reagent code and reads the approximate equation parameters, the evaluation parameters, and the test values corresponding to the combination.

[Step S6]

In step S6, the reference data creation unit 425 determines whether the data of the read approximate equation parameters, evaluation parameters, and test values is data with a flag. The data with a flag denotes that the amount of analysis of the sample to be measured is already adjusted, for example. Alternatively, the data with a flag denotes data with an alarm provided by the device. An example of the alarm includes linearity check. The linearity check is a function of checking the linearity of the absorbance change in an analysis item of the rate method. In the linearity check, the difference between the absorbance change amounts of the first half and the second half of a certain photometric range is calculated. If the difference is greater than a linearity check value designated in advance, it is determined that the line is not straight, and the alarm is provided to the data.

Another example of the alarm includes an ABS limit If the concentration or the enzyme activity value of the sample to be measured is abnormally high and is greater than the measurement available range of the reagent, the substrates or coenzymes in the reagent are all consumed before the photometric time. The absorbance value rapidly changes, and a correct measurement value cannot be obtained. Therefore, an upper or lower reaction limit value (ABS limit) of the absorbance is set, and the alarm is provided to the data when a value greater than the reaction limit value is detected. It is desirable that commercially available specimen data, such as a calibrator and a control specimen, is also data with a flag. This is because properties, such as viscosity, are different between the commercially available samples and general specimens, and the shapes of the reaction process curves may be different.

It is likely that the shape of the reaction process curve of the data with a flag is different from the shape of a normal reaction process curve. Therefore, it is likely that a normal distribution is not obtained if the data is included to create reference data. Thus, it is preferable to perform the determination in step S6 not to include the data with a flag in the reference data. The definition of the data with a flag may be preset, or the user may be able to freely select the definition. To realize the former function, the definition of the data with a flag can be stored in the storage device 12, for example. The data with a flag is not limited to the alarm, and the data with a flag can be defined according to the function of the automatic analysis device. If it is determined that the data is data with a flag in step S6, the process returns to step S5, and the approximate equation parameters, the evaluation parameters, and the test values are read. If it is determined that the data is not data with a flag in step S6, the process moves to step S7.

[Step S7]

In step S7, the reference data creation unit 425 stores the read approximate equation parameters, evaluation parameters, and test values in another area of the storage device 12.

[Step S10]

In step S10, the reference data creation unit 425 determines whether numbers of approximate equation parameters, evaluation parameters, and test values necessary to create reference data are stored. If it is determined that the necessary numbers are not stored, the reference data creation unit 425 returns to step S5 to repeat the reading and storage of the approximate equation parameters, the evaluation parameters, and the test values until the necessary numbers of data are obtained. If the reference data creation unit 425 determines that the necessary numbers of approximate equation parameters, evaluation parameters, and test values are accumulated, the processing process proceeds to S15.

[Step S15]

In step S15, the reference data creation unit 425 uses the accumulated approximate equation parameters, evaluation parameters, and test values to create a distribution map.

FIG. 8 is a diagram describing the distribution map of reference data. In FIG. 8, a horizontal axis 810 indicates an evaluation parameter A1, and a vertical axis 820 indicates an evaluation parameter Err. The evaluation parameter A1 denotes an absorbance change amount of the reaction process data in the end-point method. For example, when the approximate equation of Expression 5 is used, the evaluation parameter A1 is the same as the approximate equation parameter a1. The evaluation parameter Err indicates a mean square error of differences between the absorbance (approximate value) calculated by the approximate equation and the absorbance (actual measurement value) in the actual measurement for each time. A symbol 830 indicates coordinates of a combination of the evaluation parameters of each data.

Which evaluation parameters will be used for the vertical axis 820 and the horizontal axis 810 in the distribution map of reference data is stored in advance in the storage device 12. For example, a table including combinations of evaluation parameters suitable for the combinations of the test items and the reagent codes can be stored in the storage device 12. The reference data creation unit 425 searches the table according to the combination of the test item and the reagent code and selects a combination of evaluation parameters corresponding to the combination.

FIG. 9 shows an example of the table. A table 900 includes columns 910, 920, 930, and 940. The test items are described in the column 910. The reagent codes indicating the types of reagents are described in the column 920. Combinations of the approximate equation parameters, the evaluation parameters, or the test values are described in the columns 930 and 940. The approximate equation parameters, the evaluation parameters, or the test values corresponding to the vertical axis 820 of FIG. 8 are described in the column 930. The approximate equation parameters, the evaluation parameters, or the test values corresponding to the horizontal axis 810 of FIG. 8 are described in the column 940. The user may be able to change the content of the correspondence stored in the table 900.

[Step S20]

In step S20, the reference data creation unit 425 determines whether the reference data with the same combination of the item and the reagent code as that of the current processing target has been created in the past. If the reference data has not been created in the past, the process moves to step S25.

[Step S25]

In step S25, the reference data creation unit 425 reads all regression functions stored in the storage device 12, stored for creating the distribution map of reference data, and calculates values of parameters for approximating the regression functions to the reference data. In this embodiment, a formula for approximating the reaction process curve is defined as an "approximate equation", and a formula for approximating the distribution map of reference data is defined as a "regression function".

Linear expressions, quadratic expressions, cubic expressions, and other polynomials, as well as exponential functions, power functions, logarithmic functions, and other known functions can be prepared as the regression functions. A plurality of these functions may be combined to form a formula. Obviously, other functions can be prepared as the regression functions. An existing least-squares calculation method or the like can be used to calculate the parameters of the regression functions. Other than the calculation of the parameters of the regression functions, the reference data creation unit 425 also calculates indices for evaluating the regression accuracy. An R-square value (probability that a certain phenomenon is expressed by the regression function, or a correlation coefficient in the case of linear regression), an average value of residuals between the actual measurement values and the approximate values, a mean square value of the residuals, or the like can be used for the index. After the calculation, the display unit 440 displays the distribution map of reference data, the regression functions, and the approximate evaluation indices on the display device belonging to the computer 10.

Figure 10:
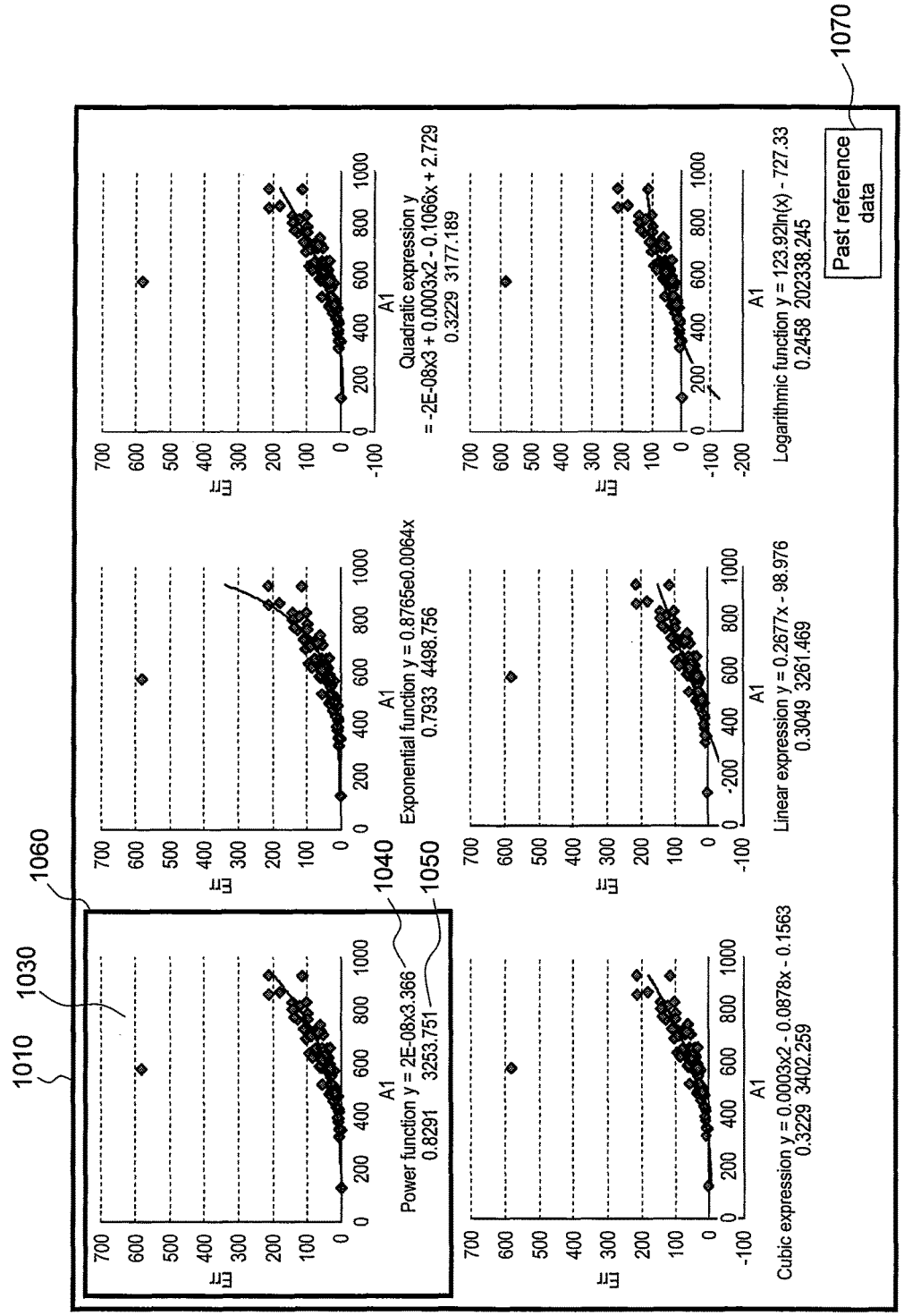
FIG. 10 is a diagram describing an example of a display screen indicating regression function candidates individually superimposed on the distribution map of reference data.

FIG. 10 shows an example of output of the results obtained by calculating the regression functions and the approximate evaluation indices in step S25, with respect to the distribution map of reference data shown in FIG. 8. A display screen 1010 displays six processing result screens corresponding to the regression functions. Each processing result screen includes: a regression function expression 1040 obtained as a result of approximating each regression function to the reference data; evaluation indices 1050 indicating the approximate accuracy; and a distribution map 1030 of reference data. In the case of FIG. 10, the indices include an R-square value and a mean square value of residuals. A curved line corresponding to the regression function expression 1040 is superimposed on the distribution map 1030 to facilitate the determination by the user.

The regression function expression 1040 with the best approximate accuracy can be visually checked on the display screen 1010. For example, the functions are displayed in the descending order of the approximate accuracy, and a frame border 1060 is placed around the processing result screen indicating the application result of the regression function with the best approximate accuracy. In the case of FIG. 10, the approximate accuracy of the processing result screens (regression functions) displayed on the upper row of the display screen 1010 is higher than the approximate accuracy of the processing result screens (regression functions) displayed on the lower row, and the approximate accuracy of the processing result screens (regression functions) displayed on the left side is higher than the approximate accuracy of the processing result screens (regression functions) displayed on the right side.

As shown in FIG. 10, a plurality of processing result screens indicating the curved lines corresponding to the regression functions superimposed on the distribution map of reference data are arranged and displayed on the same screen, and the user can compare and check on the screen the differences in the approximate accuracy due to the differences in the regression functions. As a result, the regression function reflecting the features of the distribution map of reference data can be objectively determined

[Step S30]

In step S30, the user refers to the differences between the degrees of overlapping of the curved lines corresponding to the regression function candidates obtained by the approximate process and the distribution map of reference data and refers to the evaluation values 1050 indicating the approximate accuracy of the curved lines to select the regression function expression 1040 optimal for the distribution map of reference data created in step S15. In this way, an effect of supporting the selection of the optimal regression function expression 1040 by the user can be expected from the display screen 1010.

[Step S32]

In step S32, the reference data creation unit 425 acquires the regression function selected by the user, and then the process proceeds to step S50.

[Step S35]

In step S20 described above, if the reference data creation unit 425 determines that the reference data with the same combination of the item and the reagent code as that of the current processing target has been created in the past, the process moves to step S35.

Figure 11:
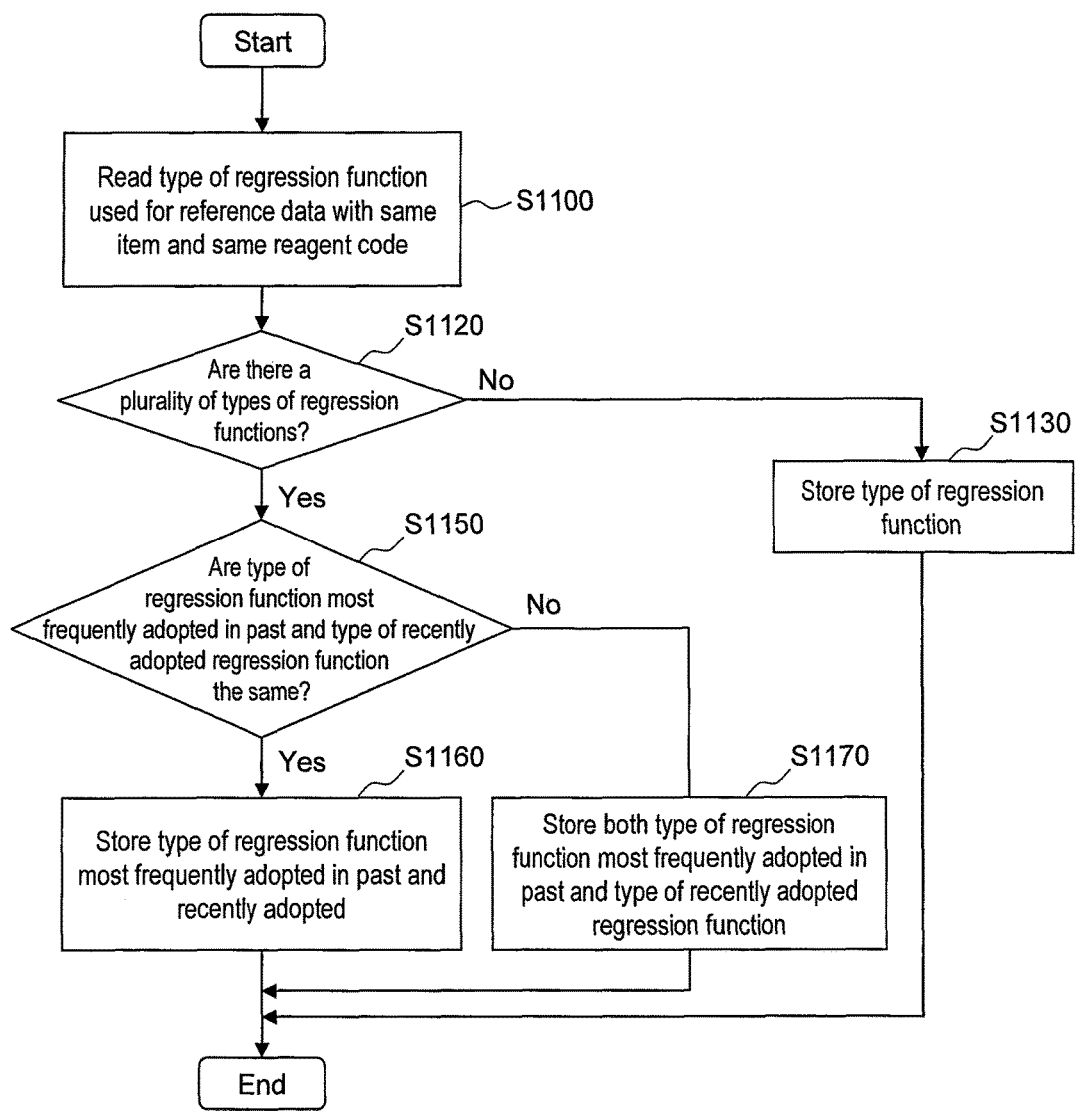
FIG. 11 is a flow chart describing an example of a processing procedure used in a selection process of a type of regression function.

In step S35, the reference data creation unit 425 selects the type of regression function. FIG. 11 is a flow chart describing the selection of the type of regression function executed in step S35.

In step S1100, the reference data creation unit 425 reads, from the storage device 12, the type of regression function used to create the reference data with the same combination of the item and the reagent code as that of the current processing target.

In step S1120, the reference data creation unit 425 determines whether there are a plurality of types of regression function. If there is one type of regression functions, the reference data creation unit 425 proceeds to step S1130 and stores the type of regression function in another area of the storage device 12.

On the other hand, if it is determined that there are a plurality of types of regression functions in step S1120, the reference data creation unit 425 proceeds to step S1150.

In step 51150, the reference data creation unit 425 determines whether the type of regression function most frequently adopted in the past and the type of regression function adopted recently are the same. If it is determined that the types are the same, the reference data creation unit 425 proceeds to step S1160 and stores the type of regression function most frequently adopted in the past and adopted recently, in another area of the storage device 12.

On the other hand, if it is determined that the types are different in step S1150, the reference data creation unit 425 proceeds to step S1170 and stores both of the type of regression function most frequently adopted in the past and the type of regression function adopted recently, in another area of the storage device 12.

[Step S40]

In step S40, the reference data creation unit 425 uses the regression function selected in step S35 to execute an approximate process of the reference data. An existing least-squares calculation method or the like can be used for the approximate calculation. As in the case of step S25, indices for evaluating the approximate accuracy may be calculated. After the approximate calculation, when the display unit 440 calculates the distribution map of reference data and the regression functions, the display unit 440 displays approximate evaluation indices on the display device belonging to the computer 10.

Figure 12:
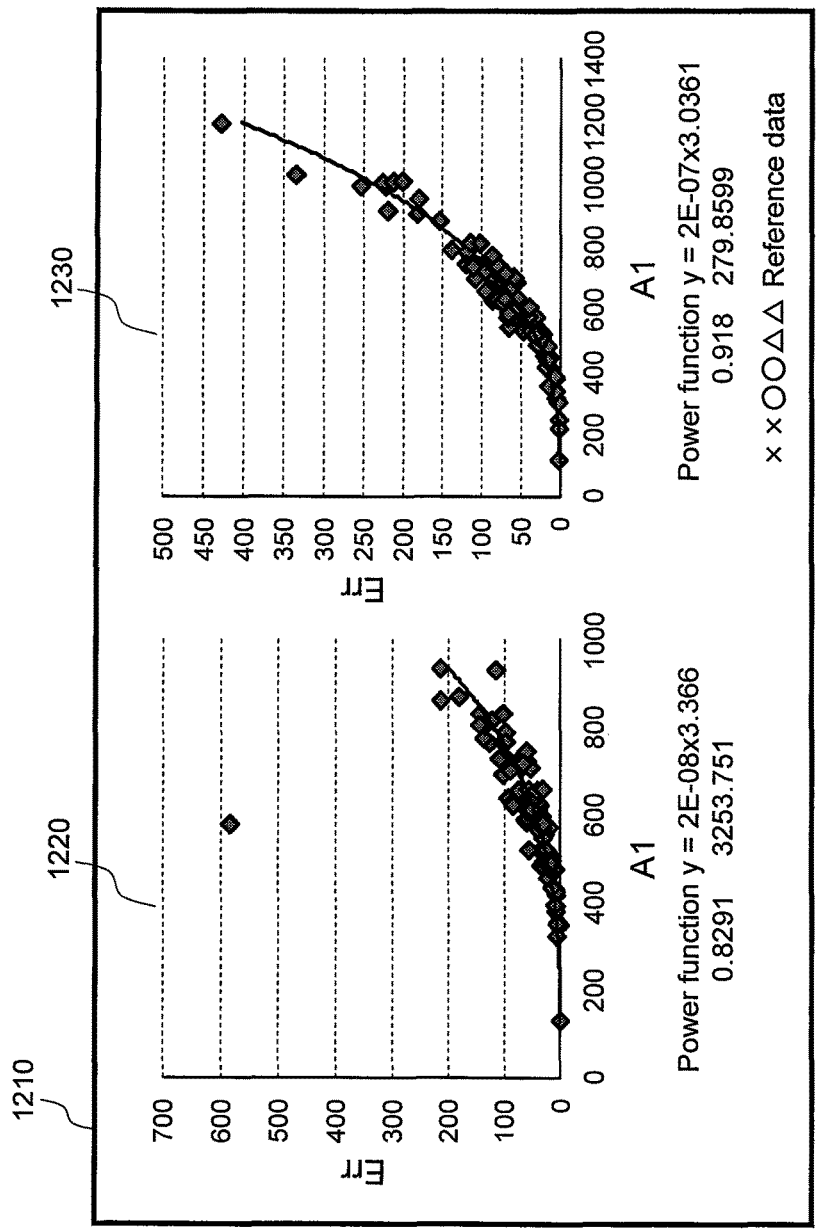
FIG. 12 is a diagram showing an example of a display screen for arranging and displaying a distribution map of reference data used in the past and a newly created distribution map of reference data.

FIG. 12 shows an example of output of the results obtained by calculating the regression functions and the approximate evaluation indices, with respect to the distribution map of reference data illustrated in FIG. 8. A distribution map 1220 of reference data calculated in step S40 and a distribution map 1230 of past reference data are displayed on a display screen 1210. Recent data can be displayed as the past reference data.

If two types of regression functions are selected in step S35, distribution maps corresponding to the types and distribution maps of data closest to the present time among the past data applying the regression functions can be displayed. The preparation of the display screen 1210 shown in FIG. 12 allows the user to evaluate the approximate accuracy of the reference data this time while referring to the distribution maps of the past reference data. This can support the user to determine an optimal regression function in the following step S45.

[Step S45]

In step S45, the user determines whether to adopt the presented regression function while referring to the approximate result. If the regression function is adopted, step S32 is executed. More specifically, the reference data creation unit 425 acquires the regression function determined by the user and then proceeds to step S50. If there are two types of regression functions in step S40, one of the regression functions is selected. In this case, in step S32, the reference data creation unit 425 acquires the regression function selected by the user and then proceeds to step S50.

On the other hand, if the user determines not to adopt the presented regression function in step S45, the reference data creation unit 425 advances to step S25 and executes the approximate process for all applicable regression functions. For the display of FIG. 10, it is desirable to be able to display the distribution map of the past reference data if the user desires. For example, a button 1070 is set on the display screen 1010. When the user presses the button 1070 on the display screen 1010, the distribution map of the past reference data as shown in FIG. 12 is displayed.

[Step S50]

In step S50, the reference data creation unit 425 stores the distribution map of reference data, the regression functions, and the approximate accuracy indices selected or determined by the user in the storage device 12.

[Step S52]

In step S52, the reference data creation unit 425 presents a screen for prompting the user to determine whether to select removal data to be excluded from the reference data. The display unit 440 displays the screen on the display device belonging to the computer 10.

[Step S55]

In step S55, the user determines whether to select removal data. If the user determines not to select removal data, the reference data creation unit 425 proceeds to step S75. On the other hand, if the user determines to select removal data, the reference data creation unit 425 proceeds to step S60.

[Step S60]

In step S60, the reference data creation unit 425 selects removal data candidates to be excluded from the reference data. The removal data candidates can be selected by using outlier relative to the parameters used in the distribution map of reference data, for example. For example, a threshold can be set for the distribution of one parameter, and the threshold can be an average value±twice as much as standard deviation ("SD"). The outlier can be data outside of the range. The thresholds are stored in advance in the storage device 12. For example, a table including thresholds suitable for the combinations of the test items, the reagent codes, and the parameters used for the reference data can be stored in the storage device 12. The reference data creation unit 425 searches the table based on the combination of the test item, the reagent code, and the parameters used for the reference data and selects the thresholds corresponding to the combination.

FIG. 13 shows an example of the table. The table 1300 includes columns 1310, 1320, 1330, and 1340. The test items are described in the column 1310. The reagent codes are described in the column 1320. The types of approximate equation parameters, evaluation parameters, or test values used to create the reference data are described in the column 1330. The thresholds for selecting the removal data candidates are described in the column 1340. The user may be able to change the content of the correspondence stored in the table 1300.

The removal data candidates selected by the reference data creation unit 425 in step S60 may be data outside of the regression function determined in step S50. The data outside of the regression function can be data outside of a value a regression value±twice as much as standard deviation, for example. The threshold is stored in advance in the storage device 12 as in FIG. 13. When the removal data candidates are selected by the method or the like, the display unit 440 displays the removal data candidates on the display device belonging to the computer 10.

Figure 14A:
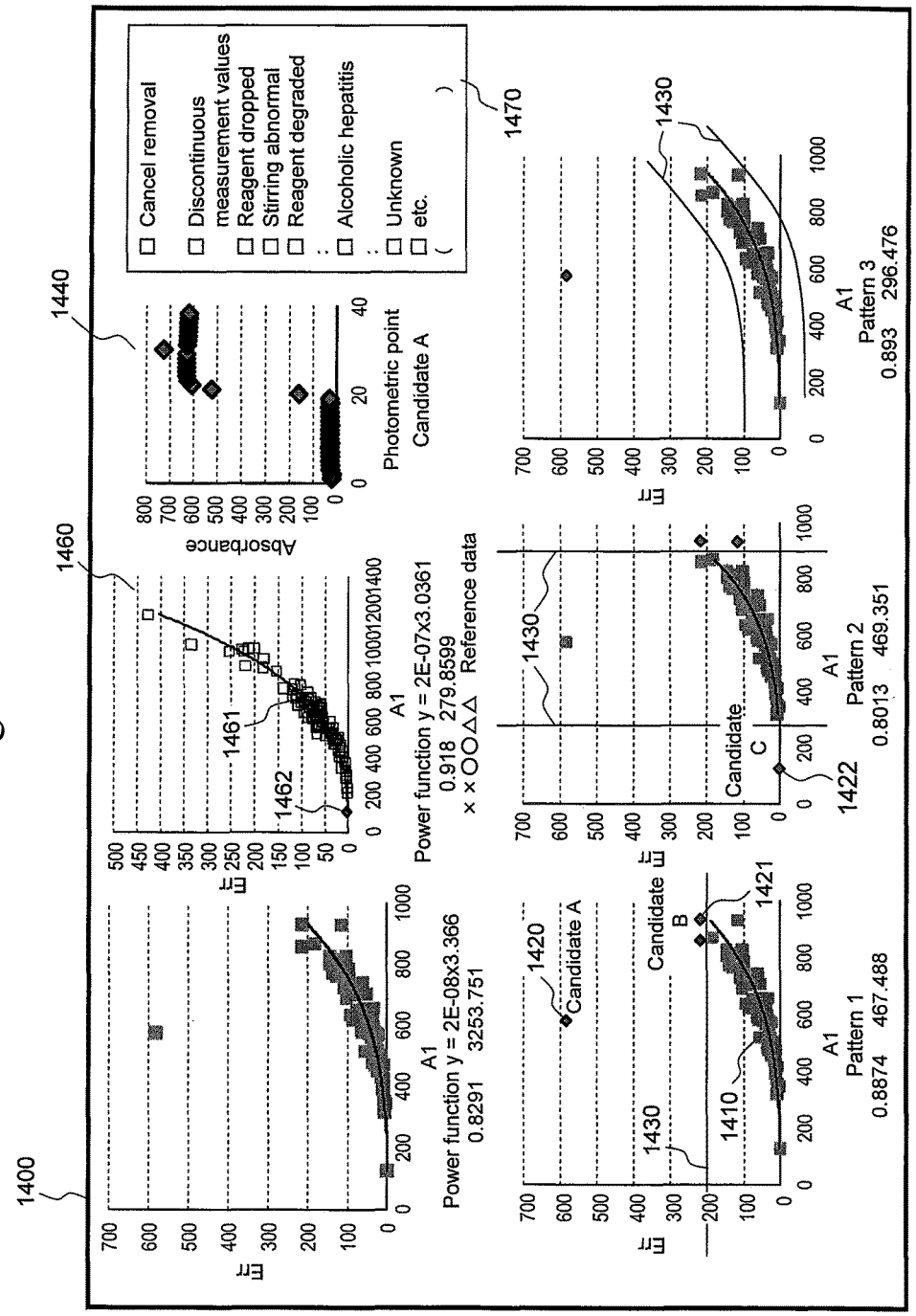
FIG. 14A is a diagram showing an example of a selection screen of removal data.

FIG. 14A shows an example of display of the removal data candidates selected in step S60. A display screen 1400 displays: a processing result screen (upper left) including the distribution map of reference data and the approximate accuracy indices before the selection of the removal data; and processing result screens (lower left, lower center, and lower right) including the distribution maps of reference data and the approximate accuracy indices corresponding to a plurality of removal methods.

How many processing result screens corresponding to the individual removal methods will be displayed may be preset, or the user may register the number of screens. Square symbols including a symbol 1410 denote original data (data to be included in the reference data), and rhombic symbols including symbols 1420, 1421, and 1422 denote removal data candidates. A range 1430 denotes a threshold for selecting data candidates to be removed from the reference data.

The processing result screen (lower left) illustrated by a pattern 1 indicates a case in which the threshold is set to a value the average value±twice as much as standard deviation for the evaluation parameter Err to select the removal data candidates. The processing result screen (lower center) illustrated by a pattern 2 indicates a case in which the threshold is set to a value the average value±twice as much as standard deviation for the evaluation parameter A1 to select the removal data candidates. The processing result screen (lower right) illustrated by a pattern 3 indicates a case in which the threshold is set to a value the regression value±twice as much as standard deviation for the regression function to select the removal data candidates. The display of the removal data candidates is not limited to these. A plurality of patterns 1 to 3 may be combined and displayed, or results of other selection methods of removal data candidates may be displayed.

If the reference data with the same combination of the item and the reagent code as that of the current processing target has been created in the past, a distribution map 1460 of past reference data (upper center) is also displayed on the display screen 1400. In that case, the distribution map 1460 is displayed to allow recognizing the data removed from the past reference data. For example, as shown in the distribution map 1460 of past reference data, data 1461 (square symbol) included in the reference data and removed data 1462 (rhombic symbol) can be distinguished by the colors or shapes of the marks.

As for the past data, the distribution map of the past reference data stored in step S50 may be displayed, or distribution maps of the entire specimen data for which the deviation determination was performed using the past reference data may be displayed. In that case, the distribution maps are displayed to allow recognizing the data determined to be deviated.

[Step S65]

In step S65, the user selects optimal removal data while checking the distribution map of reference data (upper left of FIG. 14A), the distribution maps of reference data illustrating the removal data candidates (lower left, lower center, and lower right of FIG. 14A), the distribution map of past reference data or all data for which deviation determination is performed if the map exists (upper center of FIG. 14A), and a reaction process curve of the data (upper right of FIG. 14A).

For example, in FIG. 14A, when the user clicks the symbol 1420 indicating a "removal data candidate A" on the screen, the display unit 440 displays a reaction process curve 1440 (upper right of FIG. 14A) of the removal data. Although it is preferable to display the reaction process curve 1440 on the display screen 1400, the reaction process curve 1440 may be displayed on another screen. The user can check the reaction process curve 1440 to recognize that the reaction process curve of the "removal data candidate A" includes discontinuous measurement values. The user sequentially checks the removal data candidates.

Figure 14B:
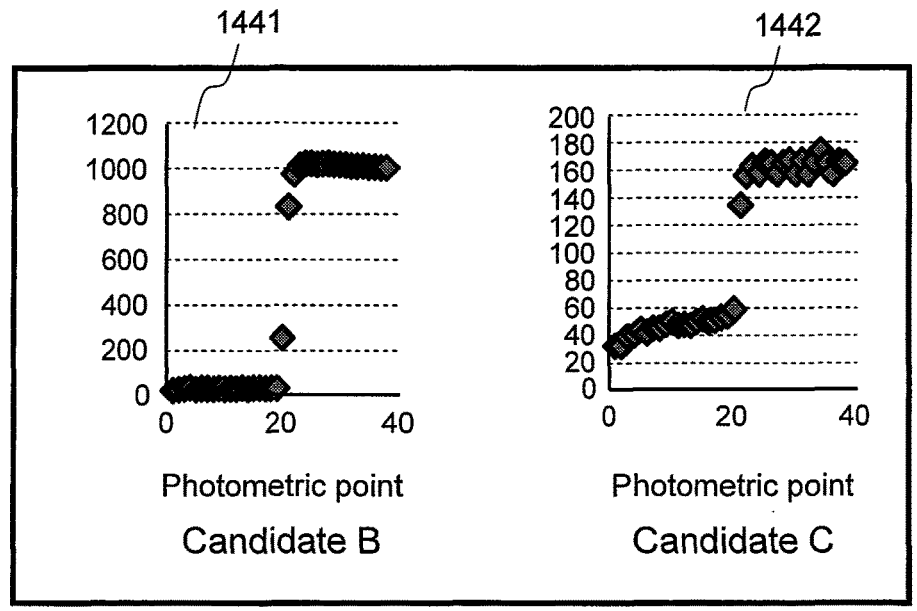
FIG. 14B is a diagram showing an example of a display screen of reaction process data corresponding to candidate points.

FIG. 14B shows an example of displaying reaction process data of a symbol 1421 indicating a "removal data candidate B" and a symbol 1422 indicating a "removal data candidate C" on a screen different from the display screen 1400. Although a reaction process curve 1441 of the "removal data candidate B" is normal, it can be recognized that the absorbance of a reaction process curve 1442 of the "removal data candidate C" is dispersed.

A plurality of reaction process curves corresponding to the removal data candidates may be displayed at the same time on the display screen 1400. How many reaction process curves will be displayed at the same time may be set in advance, or the user may be able to set the number of reaction process curves. The reaction process curves of the removal data candidates may be superimposed and displayed. In that case, the reaction process curves can be distinguished by colors or shapes of marks to allow recognizing which reaction process curve corresponds to which candidate. Regardless of whether the curves are displayed side by side or superimposed, data other than the removal candidates can be displayed at the same time.

In the description, it is assumed that the user wants to remove only the "removal data candidate A" after checking all removal data candidates. In this case, the user can select the pattern 3 among the three patterns shown in FIG. 14A.

It is assumed that the user wants to remove the "removal data candidate A" and the "removal data candidate C" after checking all removal data candidates. In this case, the user selects the pattern 3 among the three patterns shown in FIG. 14A and further clicks the data corresponding to the "removal data candidate C" on the pattern 3 to change the type of the data to removal data.

Figure 14C:
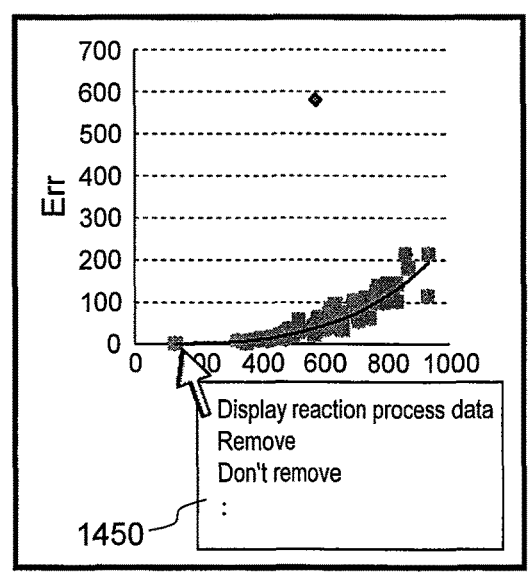
FIG. 14C is a diagram showing an example of a setting screen of removal data.

In a change method, as shown for example in FIG. 14C, a menu screen 1450 is superimposed on the original display when the user selects the target data, and the user can select individual setting items displayed on the menu screen 1450.

In FIG. 14A, a reaction process curve (graph second from the right on the upper row of FIG. 14A) corresponding to clicked data is also displayed when the user clicks data other than the removal data candidates presented by the reference data creation unit 425 on the display screen 1400. If the user wants to remove concerned data after actually checking the reaction process curve of the data, the user can change the type of the data to removal data based on the same method as in the case of FIG. 14C. Conversely, if the user wants to cancel the setting of the removal data, it is desirable to allow the user to change the data type through similar operation.

For the removal data, the user further selects or inputs a reason of removal (type of abnormality). A menu screen 1470 can be used for the selection or the input, for example. The menu screen 1470 displays selection items of possible abnormal information (derived from device, derived from reagent, or derived from specimen). The user can select or input each item when checking the removal data candidates.

The user may be able to freely set the screen configuration of the menu screen 1470. A text entry field may be arranged on the menu screen 1470 to allow the user to freely input a text.

The preparation of the display screens shown in FIG. 14A to 14C allows the user to objectively remove data from the reference data based on statistical processing. The user can select the removal data while checking the reaction process curves one by one. Therefore, it is possible to select only optimal removal data. The selection of the optimal removal data leads to an advantageous effect that highly reliable reference data can be created.

[Step S68]

In step S68, the reference data creation unit 425 acquires the removal data selected by the user.

[Step S70]

In step S70, the reference data creation unit 425 stores the removal data selected by the user and the reason of removal in the storage device 12.

[Step S75]

In step S75, the reference data creation unit 425 sets a standard range used for the deviation determination. The standard range is set so that all reference data other than the removal data selected by the user is determined to be normal. For example, the standard range is set as follows.

Residuals from the regression lines of all data included in the reference data are calculated to obtain a maximum residual value (Emax). From the residual value, Expression 10 is used to obtain n that is a regression value (Eave)±n times standard deviation (SD) which is a standard range.

$$n \geq |Emax|/SD \qquad \text{(Expression 10)}$$

The symbols || indicate an absolute value, and n can be a positive minimum value satisfying Expression 10. Alternatively, the user may preset a value ("h") of n as a standard, and n may be a positive number closest to the value h and satisfying Expression 10.

Furthermore, the standard range may be set by the following method. A residual value (Emin) with the smallest residuals from the regression line of the removal data selected by the user is obtained. From the residual value, Expression 11 is used to obtain a range of m that is a regression value (Eave)±m times standard deviation (SD) which is a standard range.

$$|Emax|/SD \leq m \leq |Emin|/SD \qquad \text{(Expression 11)}$$

The symbols || indicate an absolute value, and m is a positive number. The user can freely set m used for the standard range, from the positive numbers satisfying Expression 11.

Other than these setting methods, a range calculated from the distance between the regression function and the data included in the reference data or a range calculated from the distance between the approximate equation parameter, the evaluation parameter, or the test value used for the axis of the distribution and the data included in the reference data may be used to set the standard range.

One or a plurality of ranges may be combined to set the standard range. For example, the standard range when the user selects the "removal data candidate A" and the "removal data candidate C" as the removal data in FIG. 14A can be set using the approximate equation parameter A1 and the regression function, and the standard range can be "A1>(average value of A1−k times standard deviation) and regression value±p times standard deviation". The values k and p are positive numbers.

[Step S80]

In step S80, the reference data creation unit 425 stores the standard range to be used for the deviation determination in the storage device 12.

The reference data created in the processing procedure shown in FIG. 1 is stored in a database of the storage device 12.

Figure 22B:
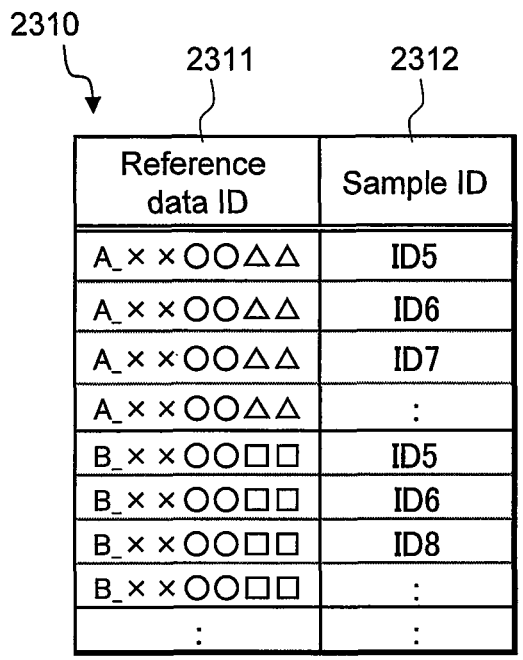
FIG. 22B is a diagram showing a table configuration for storing data included in the reference data.
Figure 22C:
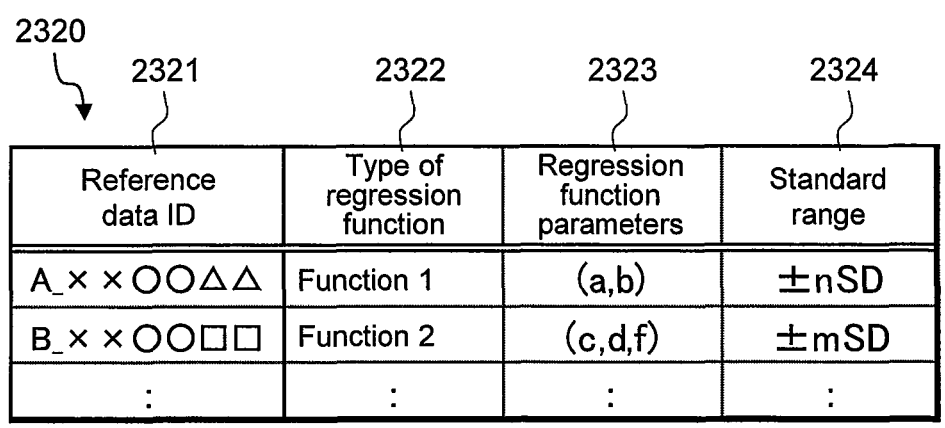
FIG. 22C is a diagram showing an example of a table configuration for storing regression functions and standard ranges of the reference data.

FIGS. 22A to 22C show an example of a configuration of the database. The database includes three tables.

A table 2300 shown in FIG. 22A is a table storing determination results of whether to include each data in the reference data and reasons for being determined as "removal data candidates". The table 2300 includes columns 2301, 2302, 2303, 2304, 2305, 2306, 2307, and 2308.

The column 2301 stores sample IDs. The column 2302 stores test items. The column 2303 stores reference data IDs. The column 2304 stores approximate equation parameter values, evaluation parameter values, or test values used for the reference data. The column 2305 stores results of the determination by the user, indicating whether to include the data in the reference data. The column 2306 stores results of the deviation determination by the user. The column 2307 stores reasons of the removal of the samples from the reference data. The column 2308 stores reasons of the deviation when the data is determined to be deviated.

The sample ID of the column 2301 is provided with an ID to uniquely identify the data. Coordinates of the horizontal and vertical axes of the approximate equation parameter values, the evaluation parameter values, or the test values used for the distribution map of reference data can be stored in the column 2304. Details of the columns 2306 and 2308 will be described later.

A table 2310 shown in FIG. 22B is a table storing reference data IDs and reference data of the reference data IDs. The table 2310 includes columns 2311 and 2312. The column 2311 stores the reference data IDs, and the column 2312 stores sample IDs of the reference data.

A table 2320 shown in FIG. 22C is a table storing regression functions of the reference data and standard ranges used for the deviation determination. The table 2320 includes columns 2321, 2322, 2323, and 2324. The column 2321 stores reference data IDs. The column 2322 stores types of regression functions. The column 2323 stores regression function parameters determined from the distribution maps of reference data. The column 2324 stores standard ranges used for the deviation determination.

[Deviation Determination Processing Procedure and Checking Process of Deviation Determination Result (FIG. 15)]

As described, the user can use the creation processing procedure of reference data shown in FIG. 1 to objectively set the creation process of reference data (creation process of distribution map, selection process of regression function curve, removal process of removal data, and setting process of standard range) that needs to be created again every time the reagent manufacturer, the lot, or the like is changed.

Figure 15:
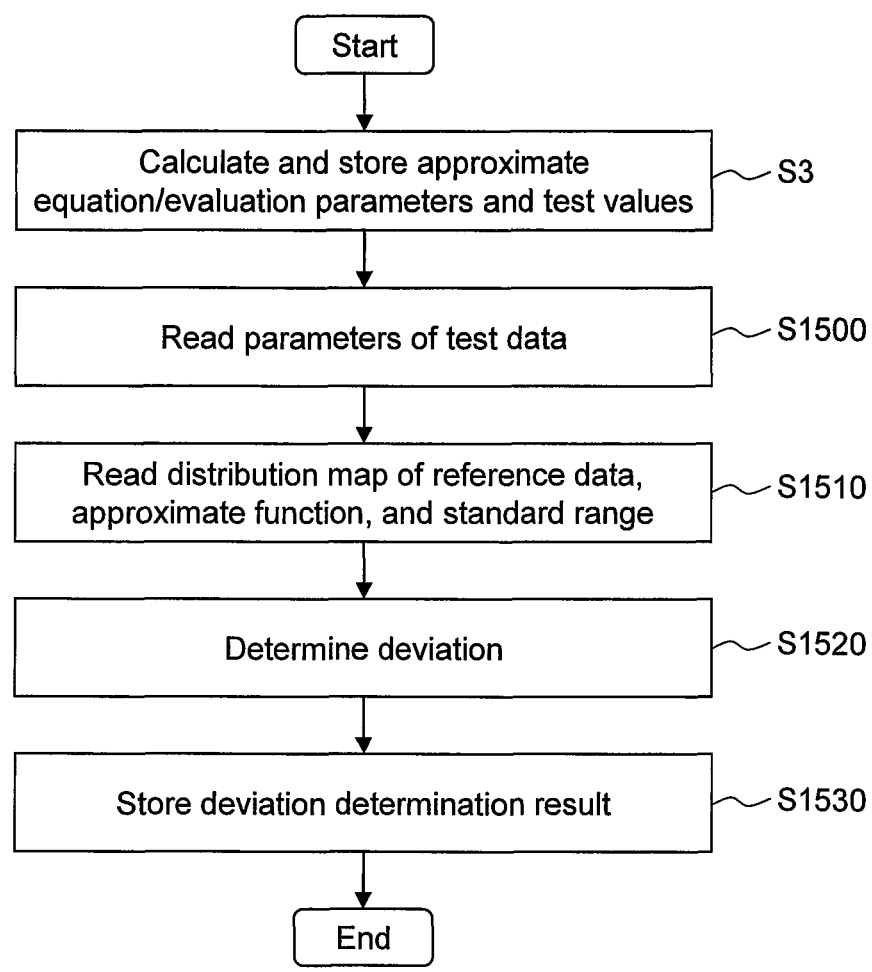
FIG. 15 is a flow chart showing a processing procedure of deviation determination.

FIG. 15 illustrates a processing procedure of determining the deviation of test data by using the created reference data, illustrating a deviation determination processing procedure and a checking processing procedure of a deviation determination result.

[Step S3]

In the process, the same process as in step S3 of FIG. 1 is executed. More specifically, the control unit 13 calculates the approximate equation parameters, the evaluation parameters, and the test values.

[Step S1500]

In step S1500, the deviation determination unit 435 reads the approximate equation parameters, the evaluation parameters, and the test values of the test data from the storage device 12.

[Step S1510]

In step S1510, the deviation determination unit 435 reads the distribution map, the regression functions, and the standard range of the reference data corresponding to the test data, from the storage device 12.

[Step S1520]

In step S1520, the deviation determination unit 435 determines the deviation of the test data. If the approximate equation parameters, the evaluation parameters, and the test values of the test data are within the standard range, the deviation determination unit 435 determines that the test data is not deviated. On the other hand, if one of the approximate equation parameters, the evaluation parameters, and the test values of the test data is out of the standard range, the deviation determination unit 435 determines that the test data is deviation data.

[Step S1530]

In step S1530, the deviation determination unit 435 stores the data determined to be deviated, in the storage device 12.

The user checks the data determined to be deviated, at the end of a day or at a timing before the test result is reported to the doctor. When the user checks the deviation data, the display unit 440 displays a deviation data checking screen on the display device belonging to the computer 10.

Figure 16A:
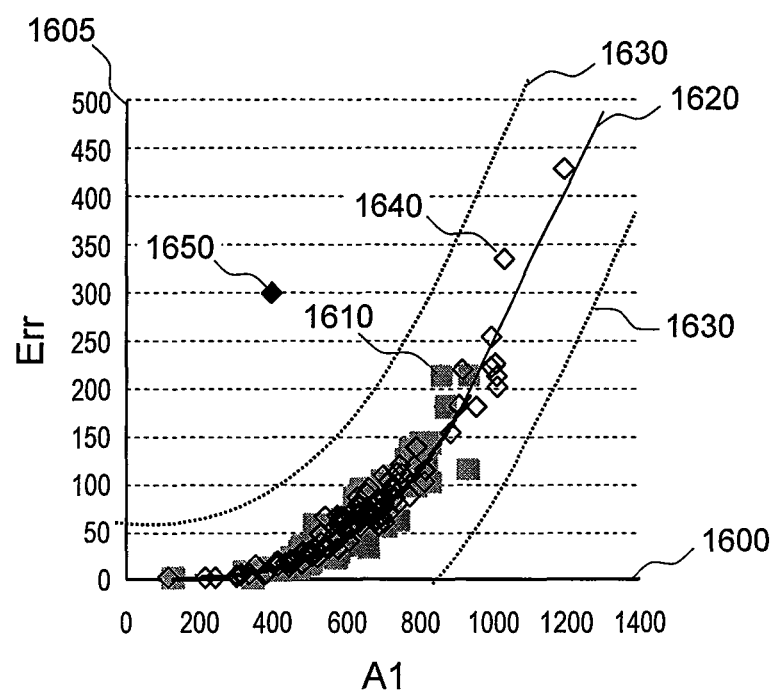
FIG. 16A is a diagram showing an example of a deviation determination screen.
Figure 16B:
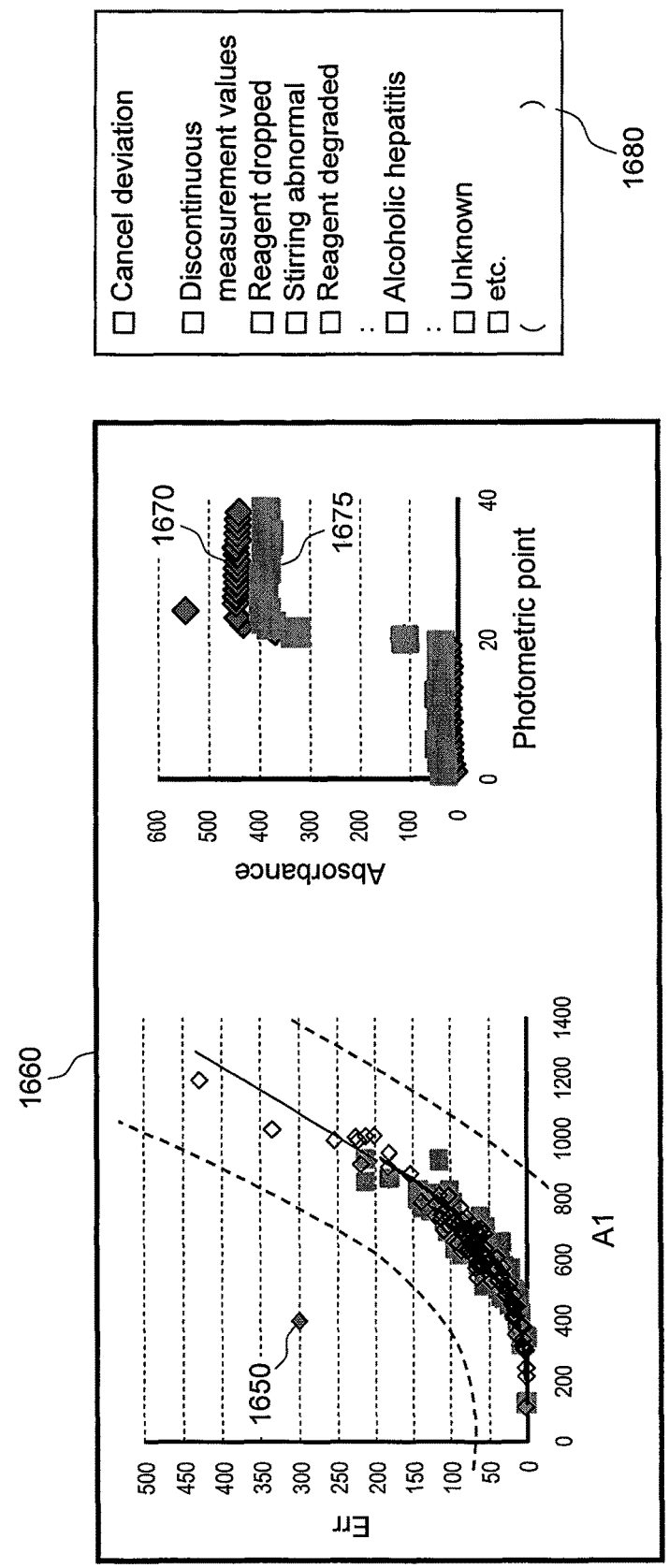
FIG. 16B is a diagram showing an example of the deviation determination screen.
Figure 16C:
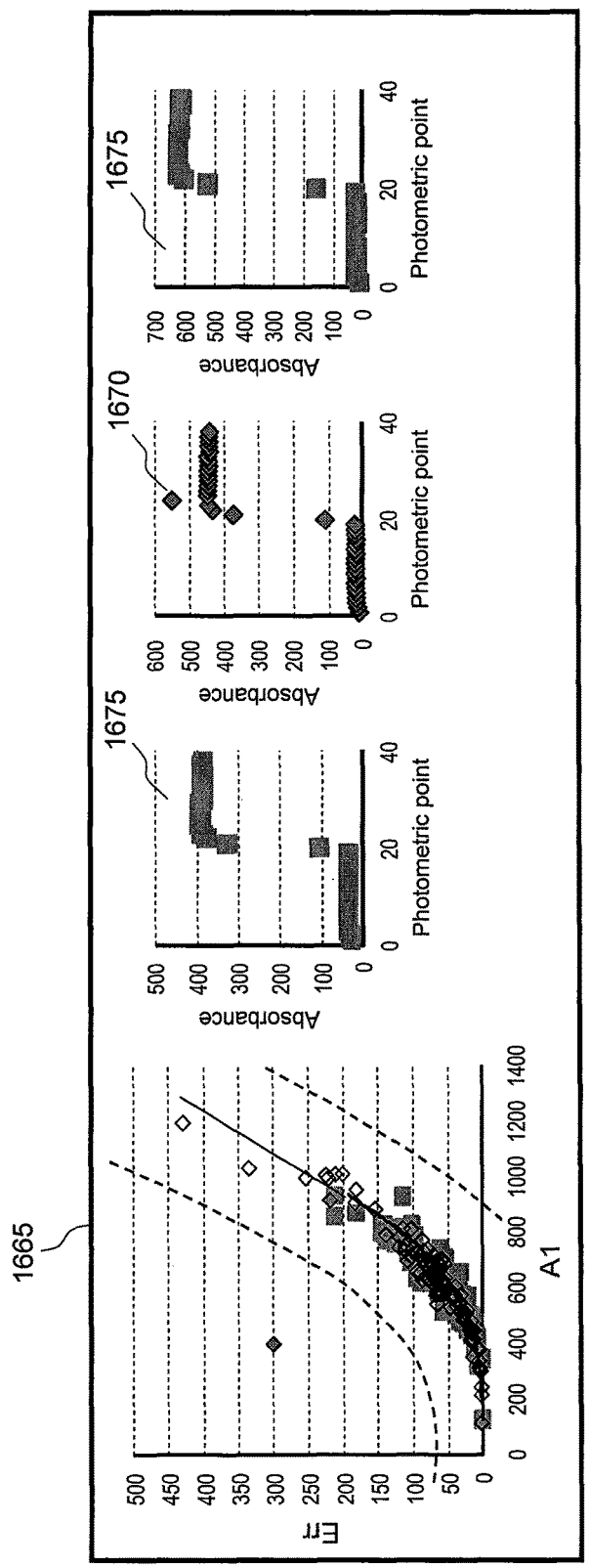
FIG. 16C is a diagram showing an example of the deviation determination screen.

FIGS. 16A to 16C show examples of the checking screen of deviation data. A horizontal axis 1600 of the display screen shown in FIG. 16A indicates the evaluation parameter A1, and a vertical axis 1605 indicates the evaluation parameter Err. A symbol 1610 indicates reference data, a function 1620 indicates a regression function of the reference data, and a range 1630 indicates a standard range.

A symbol 1640 indicates test data. A symbol 1650 indicates test data determined to be deviated. The data 1650 determined to be deviated is displayed to allow distinction from the test data 1640 within the standard range. For example, the data can be distinguished by the colors or shapes of the marks. In the case of FIG. 16A, the symbol 1640 is expressed by an outlined rhombus, and the symbol 1650 is expressed by a black rhombus. If the user selects the data determined to be deviated by click operation on the screen, the display unit 440 displays the reaction process curve of the data on the display device belonging to the computer 10.

It is preferable to display the reaction process curve on the same screen as the display screen of the corresponding deviation determination result, as in a display screen 1660 shown in FIG. 16B and in a display screen 1665 shown in FIG. 16C. However, the reaction process curve may be displayed on a different screen from the deviation determination result.

When the reaction process curve is displayed, it is desirable to superimpose and display a reaction process curve 1670 of the data determined to be deviated and a reaction process curve 1675 of the reference data or data within the standard range, as shown in the display screen 1660 (FIG. 16B). The display method can be adopted to allow the user to easily check the degree or reason of deviation of the reaction process curve determined to be deviated.

As shown in the display screen 1665 (FIG. 16C), a plurality of reaction process curves 1670 of the data determined to be deviated and reaction process curves 1675 of the reference data or the data within the standard range may be arranged and displayed on the same screen. The user may be able to freely select and display the reference data or the data within the standard range.

In the display screen 1665 (FIG. 16C), it is preferable to be able to distinguish the reaction process curves 1670 of the deviated data from the reaction process curves 1675 of the reference data or the data within the standard range. For example, the curves can be distinguished by the colors or shapes of the marks.

It is also preferable that the user can select or input the reason of the deviation for the data determined to be deviated. For example, a menu screen 1680 can be used as a screen for selection or input. Selection items of possible abnormal information (derived from device, derived from reagent, and derived from specimen) are displayed in advance on the menu screen 1680. The user can select or input each item when checking the deviation data candidates.

The screen configuration of the menu screen 1680 may be the same as the configuration of the menu 1470 shown in FIG. 14. The user can check the reaction process curve 1670 of the data determined to be deviated to check on the screen that the data includes discontinuous measurement values. In this case, the user selects "Discontinuous Measurement Values" among the items prepared in the menu screen 1680.

It is also desirable to allow the user to determine to cancel the deviation determination for the data determined to be deviated (to determine that the data is within the standard range). In this case, the process returns to step S75 of FIG. 1, and the standard range can be set again. The result of the determination by the user is stored in the storage device 12.

Like the result of the removal determination and the reason of the removal, the result of the deviation determination and the reason of the deviation are stored in the database of the storage device 12 (table shown in FIG. 22A). The column 2301 stores sample IDs. The column 2302 stores test items. The column 2303 stores reference data IDs used for the deviation determination. The column 2304 stores approximate equation parameter values, evaluation parameter values, or test values used for the deviation determination. The column 2306 stores results of the deviation determination in step S1520. The column 2308 stores reasons of deviation when the data is determined to be deviated.

[Modified Example]

An example has been described in the present embodiment in which the control unit 13 executes all processes. However, a processing device other than the control unit 13 of the automatic analysis device can be used to execute the same process. For example, the process illustrated in the first embodiment may be executed as software processing executed in the computer (PC) 10. A storage device in the computer (PC) 10 can also be used as the storage device 12.

[Conclusion]

The creation method of the reference data described in the present embodiment can be adopted to allow the user to set the reference data that needs to be created again every time the reagent manufacturer, the lot, or the like is changed (creation process of distribution map, selection process of regression function curve, removal process of removal data, and setting process of standard range) based on objective information. Optimal reference data can be created every time the reagent manufacturer, the lot, or the like is changed, and this improves the accuracy of the accuracy control.

[Second Embodiment]
[Device Configuration]

Subsequently, a device configuration and processing operation of an automatic analysis device according to a second embodiment will be described in detail with reference to the drawings. In the present embodiment, the automatic analysis device is also a biochemical automatic analysis device. Therefore, the device configuration is the same as in the first embodiment. More specifically, the device has the device configuration shown in FIG. 2. The operation other than that of the control unit 13 is the same as in the first embodiment. Therefore, the units other than the control unit 13 will not be described in detail.

[Processing Operation]

The control unit 13 according to the present embodiment executes processing operation different from the first embodiment, in relation to the (2) deviation determination processing procedure and the check processing procedure of the deviation determination result. In the present embodiment, the reference data is created for all approximate equation parameters. In the creation, the horizontal axis of the distribution map of reference data all indicates test values.

Figure 17:
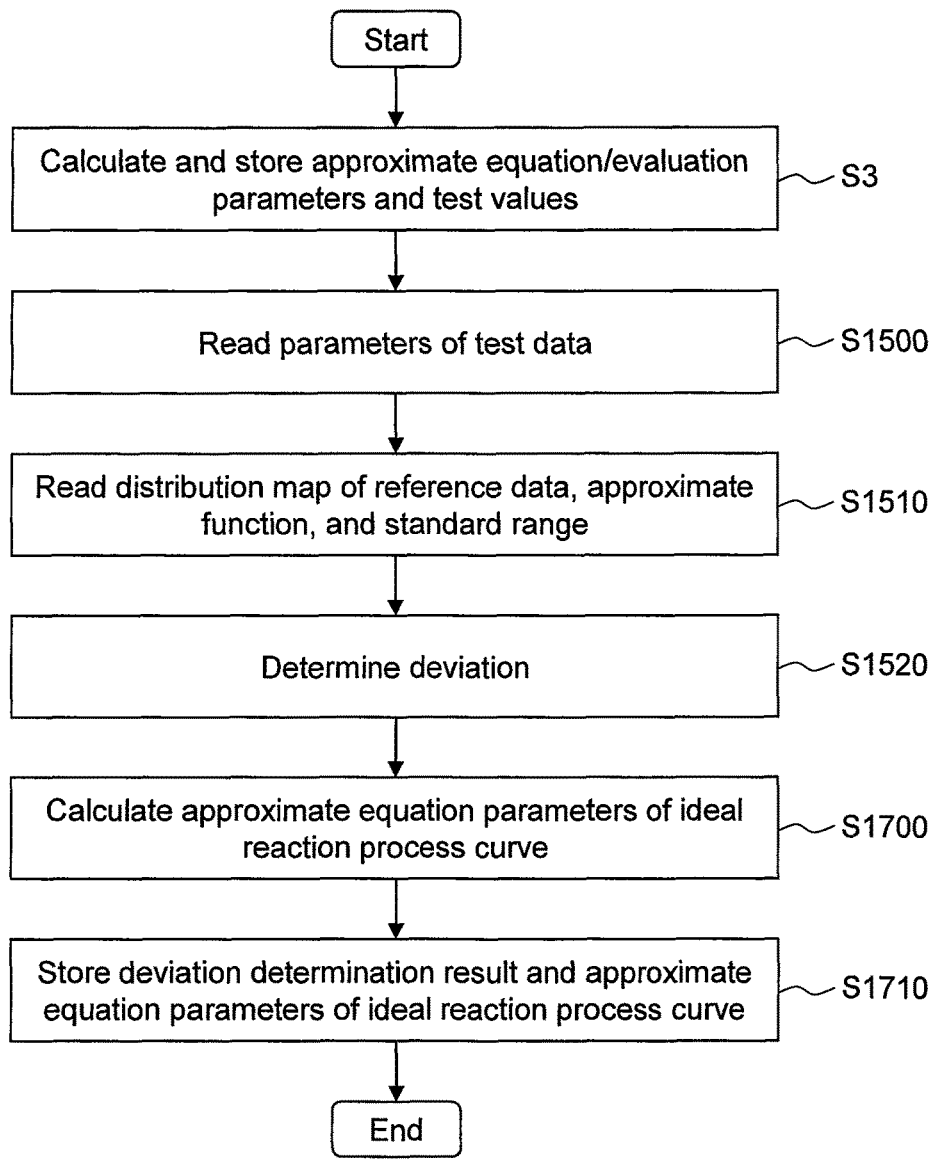
FIG. 17 is a flow chart describing a processing procedure according to a second embodiment.

FIG. 17 shows a deviation determination procedure. In FIG. 17, the processing steps corresponding to FIG. 15 of the first embodiment are designated with the same reference numerals. In the processing processes shown in FIG. 17, the processes of step S3 and steps S1500 to S1520 are the same as the processes of step S3 and steps S1500 to S1520 in FIG. 15.

In step S1700, for the data determined to be deviated, the deviation determination unit 435 calculates an approximate equation parameter of a predicted reaction process curve ("ideal reaction process curve") of a case in which the data is not deviated (within the standard value), from the regression function of the reference data.

Figure 18A:
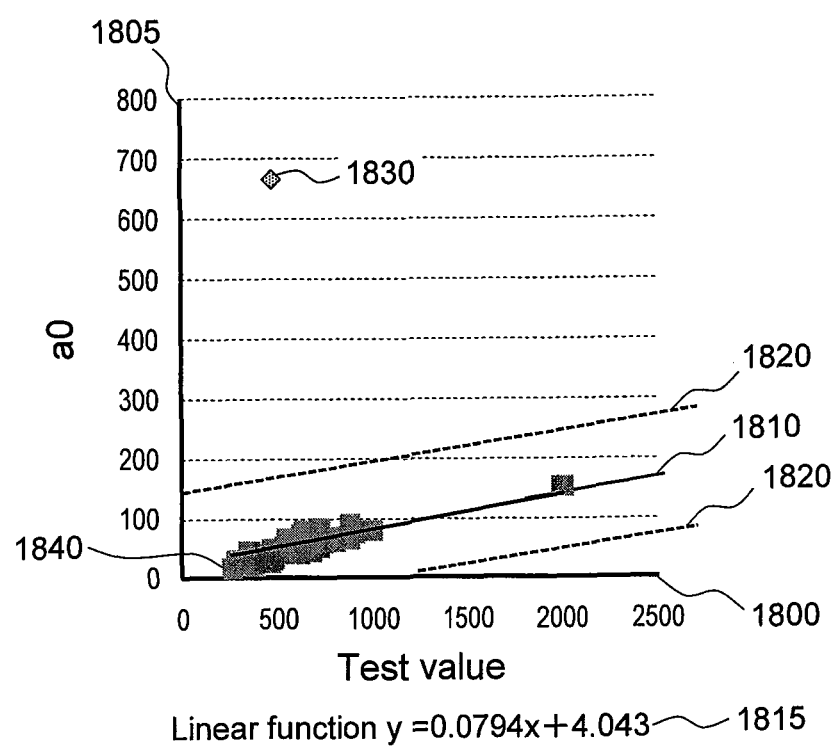
FIG. 18A is a diagram showing an example of a deviation determination screen.

FIG. 18A illustrates an example in which the approximate equation of Expression 5 is used to calculate the approximate equation parameter, and data is determined to be deviated in the reference data created by using the approximate equation parameter a0 and the test values. In the present embodiment, it is assumed that the other approximate equation parameters a1 and k are determined to be within the standard range.

In FIG. 18A, a horizontal axis 1800 indicates the test values, and a vertical axis 1805 indicates the approximate equation parameter a0. A symbol 1840 indicates reference data, and a function 1810 indicates a regression function of the reference data. A range 1820 indicates a standard range for the function 1810. A symbol 1830 indicates test data determined to be deviated. The function 1810 is expressed by a regression function expression 1815. For an arbitrary test value, the approximate equation parameter a0 indicating the ideal reaction process curve can be calculated by Expression 12 based on the approximate function expression 1815.

$$a0 \text{ of ideal reaction process curve (ideal)} = 0.0794 \times \text{text value}_{1830} + 4.043 \quad \text{(Expression 12)}$$

The test value$_{1830}$ denotes a test value of the deviation data (symbol 1830).

As described, the regression function of the reference data can be used to obtain the approximate equation parameter indicating the ideal reaction process curve. An error bar of the ideal reaction process curve is also calculated at the same time. For the error bar, dispersion (standard deviation) of the distance from the regression function of the reference data can be obtained as the dispersion of the reference data. Alternatively, the error bar may be the standard range used for the deviation determination.

In step S1710, the deviation determination unit 435 stores the determined deviation data, the approximate equation parameter indicating the ideal reaction process curve, and the error bar of the ideal reaction process curve in the storage device 12.

Figure 18B:
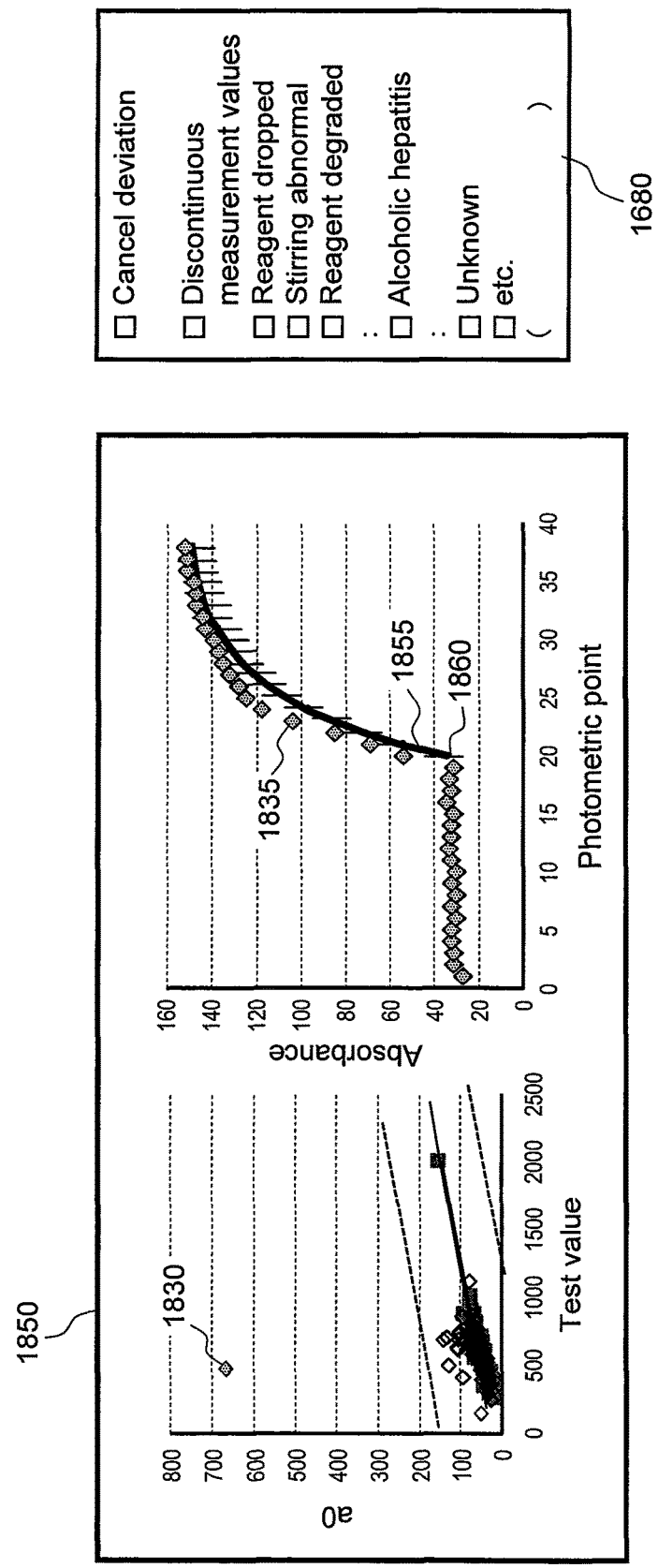
FIG. 18B is a diagram showing an example of the deviation determination screen.
Figure 18C:
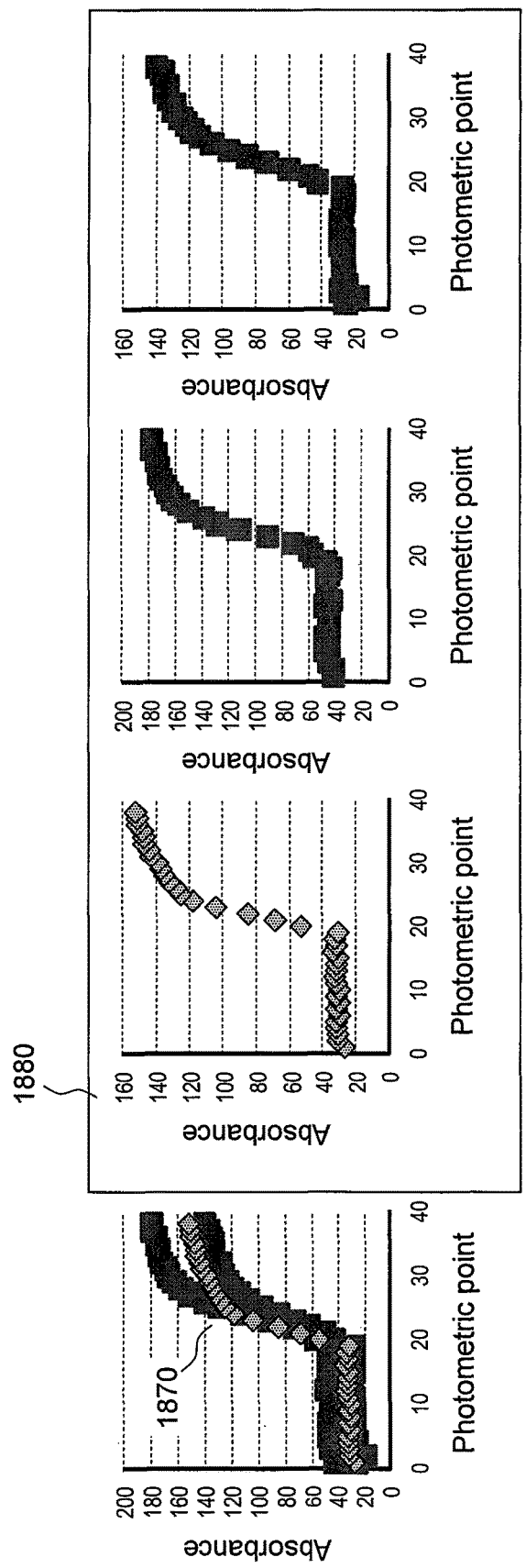
FIG. 18C is a diagram showing an example of the deviation determination screen.

The user checks the data determined to be deviated, at the end of a day or at a timing before the test result is reported to the doctor. When the user checks the deviation data, the display unit 440 displays a deviation data checking screen on the display device belonging to the computer 10. FIGS. 18B and 18C show examples of the checking screen of the deviation data. The display unit 440 displays a display screen 1850 shown in FIG. 18B on the display screen belonging to the computer 10, when the user selects the deviation data (symbol 1830) on the distribution map of reference data (left diagram). A reaction process curve 1835 corresponding to the deviation data (symbol 1830) is displayed on a right screen of the display screen 1850. More specifically, the reaction process curve 1835 is displayed on the same screen as the deviation determination result. In this way, although the deviation determination result and the reaction process curve 1835 may be displayed on the same screen, they may be displayed on different screens.

When the user instructs display of the ideal reaction process curve in the display screen 1850, the display unit 440 superimposes an ideal reaction process curve 1855 and an error bar 1860 stored in step S1710, on the reaction process curve 1835 determined to be deviated.

For example, if the deviated reaction process curve 1835 and another reaction process curve within the standard range are displayed on top of each other or side by side as indicated by a reaction process curve 1870 (left diagram of FIG. 18C)

and a reaction process curve 1880 (right diagram of FIG. 18C), it is hard to recognize the reason why the data is determined to be deviated.

However, when the ideal reaction process curve 1855 and the reaction process curve 1835 determined to be deviated are superimposed and displayed as in FIG. 18B, the reason that the data is determined to be deviated can be easily recognized. Similarly, when the error bar 1860 indicating the range that the data is determined to be not deviated and the reaction process curve 1835 determined to be deviated are superimposed and displayed, the reason that the data is determined to be deviated can be easily recognized. For example, in the case of FIG. 18B, it can be recognized that the reaction process curve 1835 determined to be deviated has a feature that the baseline of the first half of the reaction process is increasing.

It is also desirable that the user can freely select or input the reason of the deviation for the data determined to be deviated. For example, the menu screen 1680 can be used as a screen for selection or input. Selection items of possible abnormal information (derived from device, derived from reagent, and derived from specimen) are displayed in advance on the menu screen 1680. The user can select or input each item when checking the deviation data candidates.

The screen configuration of the menu screen 1680 can be the same configuration as the menu screen 1470 shown in FIG. 14. The result determined by the user is stored in the storage device 12.

The processing method described in the present embodiment can be adopted to create an ideal reaction process curve for each test item, reagent code, and reagent lot. The display of the ideal reaction process curve and the reaction process curve of the data determined to be deviated, in a form that allows comparison, facilitates the check of the reason of the deviation by the user.

[Third Embodiment]
[Device Configuration]

Subsequently, a device configuration and processing operation of an automatic analysis device according to a third embodiment will be described in detail with reference to the drawings. In the present embodiment, the automatic analysis device is also a biochemical automatic analysis device. Therefore, the device configuration is the same as in the first embodiment. More specifically, the device has the device configuration shown in FIG. 2. The operation other than that of the control unit 13 is the same as in the first embodiment. Therefore, the units other than the control unit 13 will not be described in detail.

[Processing Operation]

The control unit 13 according to the present embodiment executes the (3) processing procedure of creating a distribution map of normal data and abnormal data.

Figure 19A:
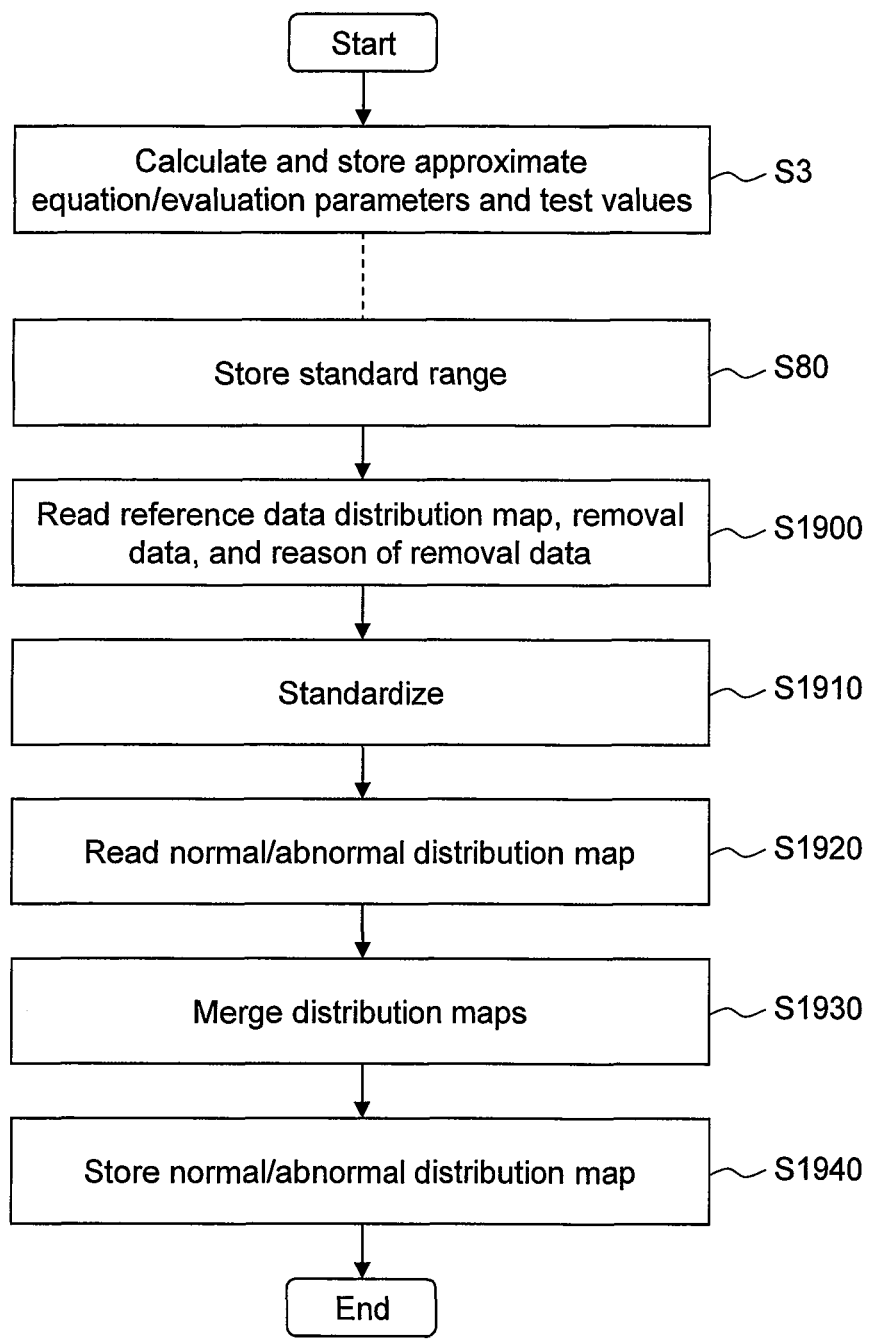
FIG. 19A is a flow chart describing a processing procedure according to a third embodiment.
Figure 19B:
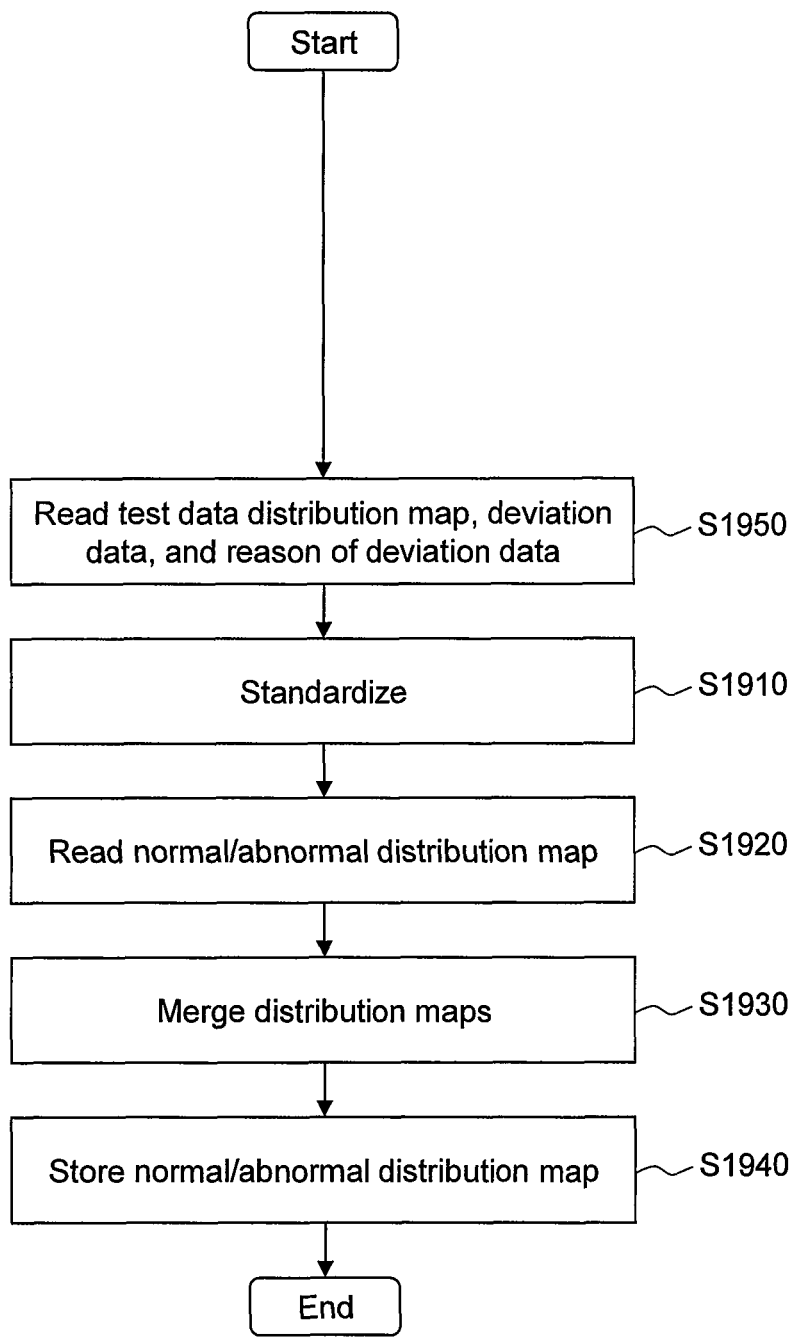
FIG. 19B is a flow chart describing a processing procedure according to the third embodiment.

FIGS. 19A and 19B show the creation procedure of the distribution map. The processes of steps S3 to S80 of the processing processes shown in FIG. 19A are the same processes as steps S3 to S80 in FIG. 1.

In step S1900, the normal/abnormal distribution map creation unit 445 reads the distribution map 1220 of reference data, the regression function of reference data, the removal data, and the reason information of the removal data from the database stored in the storage device 12.

In step S1910, the normal/abnormal distribution map creation unit 445 standardizes the distribution map 1220 of reference data read in step S1900. Standardization of a normal distribution can be used for the standardization.

Figure 20A:
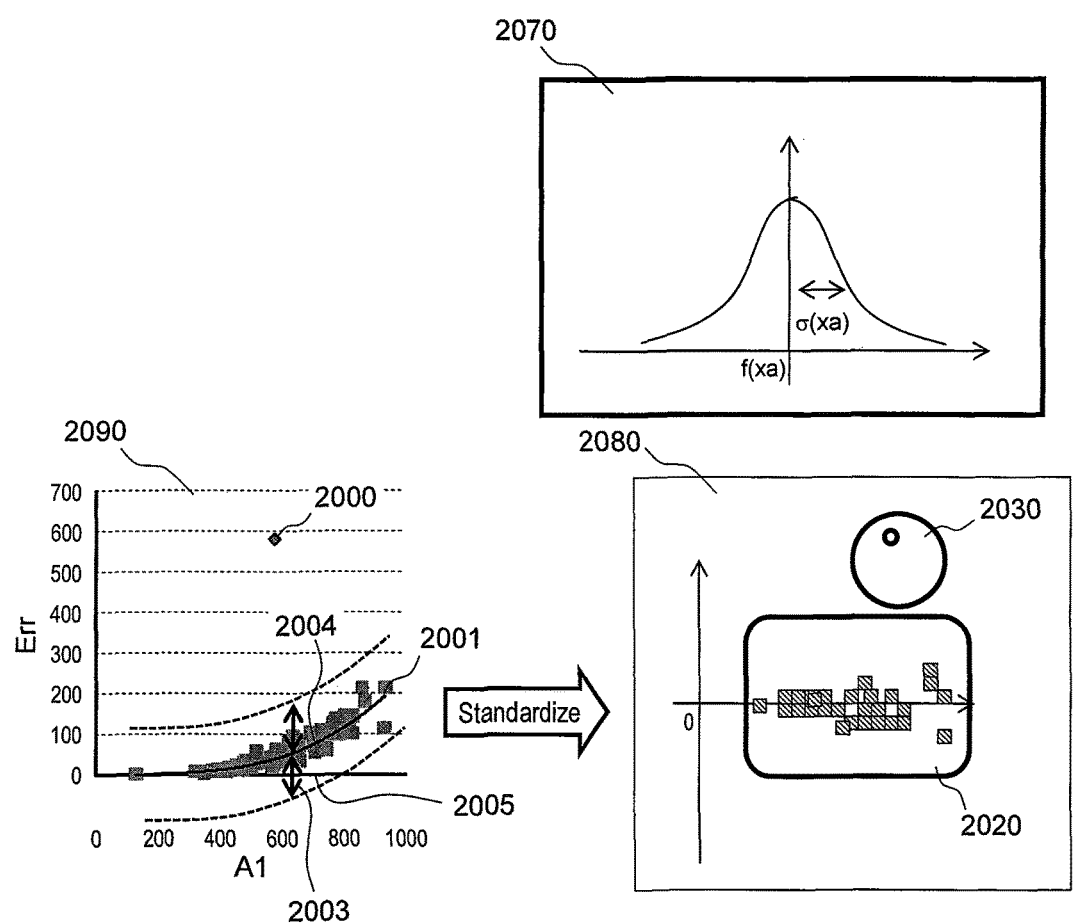
FIG. 20A is a diagram showing an example of display of a normal/abnormal distribution map.

FIG. 20A shows a concept and method of the standardization. It is assumed here that a regression function 2001 of a distribution map 2090 of reference data is provided by y=f(x). It is also assumed that a standard range 2003 is provided by σ(x). A regression value 2004 (f(xa)) with a value 2005 (A1=xa) follows a normal distribution 2070. The normal distribution 2070 is expressed by (f(xa), σ(xa)).

The standardization can be expressed by Expression 13.

$$Ya=(ya-f(xa))/\sigma(xa) \qquad \text{(Expression 13)}$$

As a result of the standardization, the normal distribution 2070 follows a standard normal distribution N (0, 1). Similarly, when all data illustrated in the distribution map 2090 of reference data is standardized, the distribution is converted to a standardized distribution map 2080. As shown in the standardized distribution map 2080, the data included in the reference data is distributed as normal data in a frame indicated by a symbol 2020, and removal data indicated by a symbol 2000 is distributed as abnormal data in a frame indicated by a symbol 2030. The range of the frame indicated by the symbol 2020 and the range of the frame indicated by the symbol 2030 do not overlap. As a result of the standardization, the normal data and abnormal data form different colonies.

In step S1920, the normal/abnormal distribution map creation unit 445 reads, from the storage device 12, the distribution map using axes of the same item, the same reagent code, the same approximate equation parameters, evaluation parameters, and test values as well as the distribution map of normal data and abnormal data with the same type of regression function. If there is no corresponding distribution map, the process moves to step S1940.

In step S1930, the normal/abnormal distribution map creation unit 445 merges the standardized data with the distribution map of normal data and abnormal data.

In step S1940, the normal/abnormal distribution map creation unit 445 stores the merged distribution map of normal data and abnormal data (normal/abnormal distribution map) in the storage device 12.

The same process is also applied to the test data determined to be deviated. FIG. 19B shows a processing process applied to the test data. When the user checks the deviation results in the display screens shown in FIGS. 16A to 16C and 18A to 18C and registers deviation data and deviation reason information, the process moves to step S1950 at the same time as the registration.

In step S1950, the normal/abnormal distribution map creation unit 445 reads the test data distribution map, the deviation data, and the reason information of the deviation data from the database stored in the storage device 12. The distribution map of test data denotes a cluster of data determined to be not deviated. The processes of steps S1910 to S1940 are the same as the processes of steps 1910 to 1940 shown in FIG. 19A.

Figure 20B:
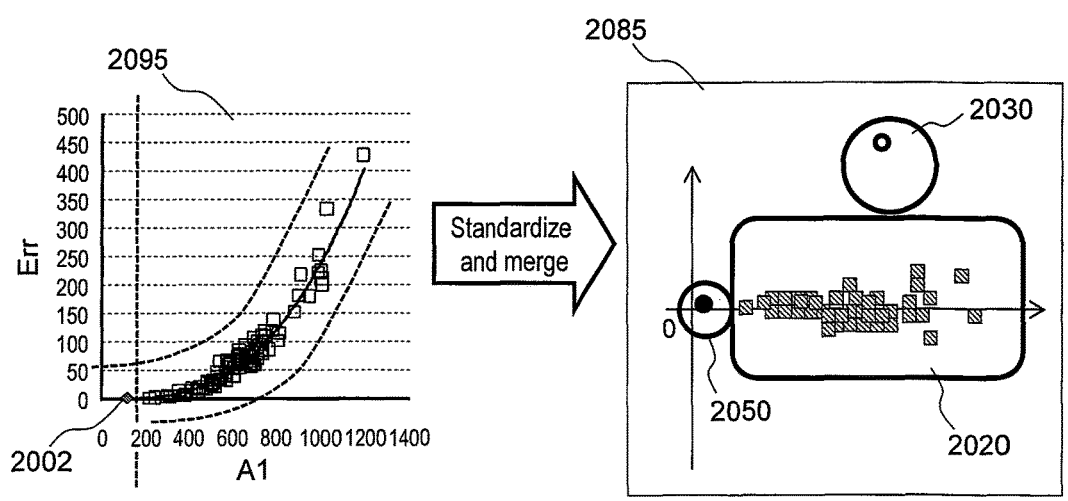
FIG. 20B is a diagram showing an example of display of the normal/abnormal distribution map.

FIG. 20B shows an example of merger of the distribution map of normal data and abnormal data. The distribution map 2090 of reference data (FIG. 20A) and a distribution map 2095 of test data (FIG. 20B) are distribution maps using axes of the same item, the same regent type, and the same evaluation parameter, and the type of the regression function is also the same. However, the lots of the reagent are different, and it is assumed that reference data is created by using different data clusters.

The distribution map 2090 of reference data (FIG. 20A) is already standardized, and the standardized distribution map 2080 of normal data/abnormal data is created. Meanwhile, when the distribution map 2095 of test data (FIG.

20B) is created, the process shown in FIG. 19B is executed, and the distribution map 2095 of test data is merged with the standardized distribution map 2080 (FIG. 20A).

A standardized distribution map 2085 (FIG. 20B) indicates the distribution map after the merger. After the merger, the normal data of the distribution map 2095 of test data is distributed in a frame provided with the symbol 2020. Meanwhile, removal data 2002 of the distribution map 2095 of test data is distributed as abnormal data in a third frame provided with a symbol 2050. In the merger, the normal data can be merged with the same mark for all data. The removal data and the deviation data can be distinguished by marks according to the reason information of removal or deviation (type of abnormality). For example, the data can be distinguished by the colors or shapes of the marks.

Figure 21:
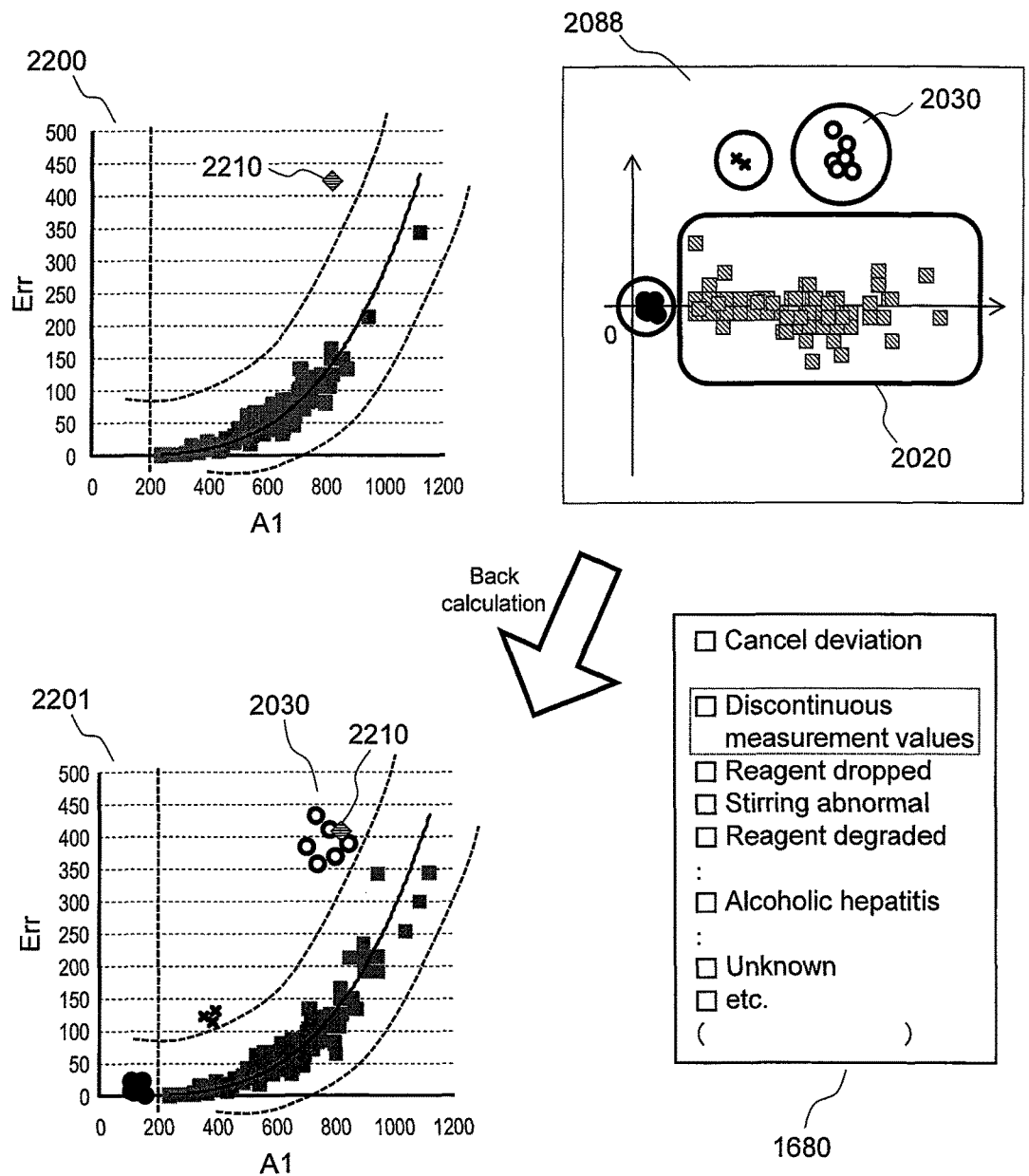
FIG. 21 is a diagram showing an example of a deviation determination screen.

FIG. 21 shows a usage of the distribution map of normal data/abnormal data created by continuously accumulating normal data and abnormal data after the reference data is created again due to a change in the reagent lot or the like. It is assumed here that the user checks a deviation determination result of a latest distribution map 2200 of test data.

When the user instructs display of the distribution map of normal data/abnormal data, the display unit 440 displays a standardized distribution map 2088 of normal data/abnormal data (upper right in FIG. 21) corresponding to the distribution map 2200 of test data (upper left in FIG. 21) on the display device belonging to the computer 10.

The normal/abnormal distribution map creation unit 445 further applies arithmetic processing opposite the standardization to all data of the distribution map 2088 of normal data/abnormal data and superimposes the distribution of normal data and the distribution of abnormal data on the latest distribution map of test data. A distribution map 2201 (lower left in FIG. 21) indicates an example of the display result.

Deviation data (symbol 2210) of the latest test data is posited at the abnormal data distribution (symbol 2030) of the distribution map 2201. Therefore, it is likely that the reason of deviation is the same as the abnormal data distribution (symbol 2030). An existing pattern recognition technique can be used to determine the position of the test data on the distribution map. When the user who has received the determination result clicks and selects the deviation data (symbol 2210) on the screen, the menu screen 1680 is displayed.

In this case, the menu screen 1680 is displayed to allow recognizing the most likely reason of deviation (type of abnormality). For example, the likely item can be "displayed on the top", "flashed", or "displayed by a different font".

As shown in FIG. 21, the distribution map of normal data/abnormal data generated by the standardization can be used to superimpose the distribution of the normal data and the distribution of the abnormal data on the newly created reference data (test data). The distribution of abnormal data can be displayed for each reason (type) of abnormality. Therefore, the type of abnormality of the deviation data can also be specified.

[Modified Example]

An example has been described in the present embodiment in which the control unit 13 executes the processes shown in FIGS. 19A and 19B. However, a processing device other than the control unit 13 of the automatic analysis device can be used to execute the same processes. For example, the process illustrated in the third embodiment can be executed as software processing executed in the computer (PC) 10. A storage device in the computer (PC) 10 can also be used as the storage device 12.

[Conclusion]

As in the processing method described in the present embodiment, the distribution map of reference data changed due to the reagent lot or the like and the distribution map of test data can be merged into one distribution map by standardizing the distribution maps based on the normal distribution. This allows continuous accumulation of data even if the reference data is created again. As a result, an accurate distribution map of normal data/abnormal data can be created.

Furthermore, the removal reason information when data is removed at the creation of the reference data and the deviation reason information of the deviation data after the deviation determination are accumulated at the same time. As a result, the distribution map of abnormal data can be created for each reason (type) of abnormality. Using the distribution map of normal data/abnormal data can superimpose the distributions of normal data and abnormal data on the newly created distribution map of test data.

As for the distribution of abnormal data, the distribution data can be superimposed and displayed for each type of abnormality. As a result, the type of abnormality of the deviation data can also be specified.

[Modified Example]

The present invention is not limited to the embodiments, but includes various modified examples. For example, the embodiments have been described in detail to facilitate understanding of the present invention, and the embodiments are not limited to the ones including all configurations described above. Part of an embodiment can be replaced by a configuration of another embodiment, and a configuration of an embodiment can be added to a configuration of another embodiment. Another configuration can be added to part of a configuration of each embodiment, or the part can be deleted or replaced.

Part or all of the configurations, functions, processing units, processing means, and the like may be realized by integrated circuits or other hardware, for example. A processor may interpret and execute programs for realizing the functions to realize the configurations, the functions, and the like. More specifically, the configurations, the functions, and the like may be realized as software. Information of programs, tables, files, and the like for realizing the functions can be stored in a storage device, such as a memory, a hard disk, and an SSD (Solid State Drive), or in a storage medium, such as an IC card, an SD card, and a DVD.

Control lines and information lines considered necessary for the description are illustrated, and not all control lines and information lines necessary in a product are illustrated. In reality, it can be considered that almost all configurations are connected to each other.

INDUSTRIAL APPLICABILITY

In general events, once data is collected to create reference data used for deviation determination, the same reference data can be continuously used in many cases. However, the shapes of the reaction process curves obtained from the measurement by an automatic analysis device may be different depending on the used reagent (manufacturer, homemade, or lot), even if the test items are the same. Therefore, the reference data needs to be created again every time the reagent manufacturer, the lot, or the like is changed.

However, in the automatic analysis device described in the first embodiment, the user can observe a plurality of processing result screens for superimposing and displaying the regression function candidates and the reference data at the same time on the same screen, even if the reference data needs to be created again due to a change in the reagent manufacturer, the lot, or the like. Therefore, the user can objectively select a regression function candidate to be applied to the reference data. The user can also objectively determine whether to remove specific data from the reference data or to determine that the data is deviated, while checking the reaction process curve of the data to be determined Therefore, the accuracy of the accuracy control can be improved.

In the automatic analysis device described in the second embodiment, an ideal reaction process curve of a test value can be created for each test item, reagent manufacturer, and lot. The user can easily check the reason of the deviation by comparing the ideal reaction process curve and the data determined to be deviated. Therefore, the load of the deviation determination by the user is reduced.

To determine the type of abnormality of the deviation data, distributions of abnormality for all types of abnormality are necessary. However, the frequency of appearance of abnormality is significantly low, and there are a wide variety of types of abnormality, such as an abnormality derived from a patient, an abnormality derived from a device, and an abnormality derived from a reagent. Therefore, the data needs to be accumulated for a long time to increase the determination accuracy. However, in an automatic analysis device, the prerequisite distribution is changed due to a change in the reagent lot or the like as described above. After all, there is a problem that creating a distribution map of abnormal data is difficult in a period in which the distribution shape does not change.

On the other hand, the automatic analysis device described in the third embodiment can create a distribution map of abnormal data that can be continuously used, even if the distribution of abnormality is changed due to the reagent lot or the like. The automatic analysis device described in the third embodiment can further specify the type of abnormality by pattern recognition using the distribution map of accumulated normal data/abnormal data. This can reduce the load of determination of deviation data or the like by the user. This can further contribute to maintaining the performance of the automatic analysis device and supporting diagnosis of a specimen of a patient.

REFERENCE SIGNS LIST

1: sample disk, 2: reagent disk, 3: reaction disk, 4: reaction tank, 5: specimen sampling mechanism, 6: pipetting mechanism, 7: stirring mechanism, 8: photometric mechanism, 9: cleaning mechanism, 10: computer (PC), 12: storage device, 13: control unit, 14: piezoelectric element driver, 15: stirring mechanism controller, 16: sample container, 17: circular disk, 18: reagent container, 19: circular disk, 20: cooling box, 21: reaction vessel, 22: reaction vessel holder, 23: drive mechanism, 24: sampling probe, 25: bearing shaft, 26: arm, 27: reagent dispensing probe, 28: bearing shaft, 29: arm, 31: fixation portion, 33: nozzle, 34: vertical drive mechanism, 110: horizontal axis (passage of time), 120: vertical axis (absorbance), 210: curved line (curved line indicating absorbance calculated by approximate equation), 220: straight line (straight line to which curved line with approximated reaction process data is asymptotic), 230: point (time that the curved line 210 with approximated reaction process data is sufficiently asymptotic to the straight line 220), 410: absorbance data acquisition unit, 415: test value calculation unit, 420: approximate equation/evaluation parameter calculation unit, 425: reference data creation unit, 435: deviation determination unit, 440: display unit, 445: normal/abnormal distribution map creation unit, 450: data bus, 500: table, 510: column (test item), 520: column (type of reagent), 530: column (type of approximate equation), 700: table, 710: column (test item), 720: column (type of reagent), 730: column (type of evaluation parameter), 810: horizontal axis (parameter value), 820: vertical axis (parameter value), 830: symbol (coordinates of combination of values of parameters of data), 900: table, 910: column (test item), 920: column (type of reagent), 930: column (type of approximate equation parameter, evaluation parameter, and test value used for deviation determination), 940: column (type of approximate equation parameter, evaluation parameter, and test value used for deviation determination), 1010: display screen (approximate result of reference data distribution map), 1030: distribution map of reference data, 1040: regression function expression (regression function of reference data distribution map), 1050: evaluation value (correlation coefficient and error), 1060: frame border (optimal reference data distribution map), 1070: button (button for displaying distribution map of past reference data), 1210: display screen (distribution map of reference data being created and distribution map of reference data created in the past), 1220: distribution map (distribution map of reference data being created), 1230: distribution map (distribution map of reference data created in the past), 1300: table, 1310: column (test item), 1320: column (type of reagent), 1330: column (type of approximate equation/evaluation parameter and test value used to create reference data), 1340: column (threshold for selecting removal data), 1400: display screen (reference data distribution map, removal data candidate, distribution map of past reference data, reaction process curve of removal data candidate, and menu for removal data), 1410: symbol (data included in reference data), 1420: symbol (removal data candidate A), 1421: symbol (removal data candidate B), 1422: symbol (removal data candidate C), 1430: threshold (threshold for selecting removal data), 1440: reaction process curve (reaction process curve of removal candidate A), 1441: reaction process curve (reaction process curve of removal candidate B), 1442: reaction process curve (reaction process curve of removal candidate C), 1450: menu screen, 1460: distribution map (distribution map of past reference data), 1461: symbol (data included in past reference data), 1462: symbol (data removed from past reference data), 1470: menu screen (removal reason selection screen), 1600: horizontal axis (parameter value), 1605: vertical axis (parameter value), 1610: symbol (reference data), 1620: function (regression function of reference data distribution map), 1630: range (standard range), 1640: symbol (test data), 1650: symbol (test data determined to be deviated), 1660, 1665: display screens (reference data, test data distribution map/reaction process curve), 1670: reaction process curve (reaction process curve determined to be deviated), 1675: reaction process curve (reaction process curve within standard range), 1680: menu screen (removal reason selection screen), 1800: horizontal axis (test value), 1805: vertical axis (parameter value), 1810: function (regression function of reference data distribution map), 1815: regression function expression (regression function expression of reference data distribution map), 1820: range (standard range), 1830: symbol (test data determined to be deviated), 1835: reaction process curve (reaction process curve determined to be deviated), 1840: symbol (reference data), 1850: display screen (reference data, test data distribution map/reaction process curve), 1855: reaction process curve (ideal reaction process curve), 1860: error bar, 1870: reaction process curve (superimposed), 1880: reaction process curve (displayed side by side), 2000: symbol (data determined to be deviated), 2002: symbol (data determined to be deviated), 2020: symbol (data determined to be normal), 2030, 2040, and 2050: symbols (distributions of data determined to be deviated), 2080: standardized distribution map (normal/abnormal distribution map), 2085: standardized distribution map (after merger), 2088: standardized distribution map (after merger), 2090: distribution map (distribution map of reference data and test data), 2095: distribution map (distribution map of test data), 2200: distribution map (distribution map of test data), 2210: symbol (data determined to be deviated), 2201: distribution map (distribution map of test data on which distribution map of converted normal data/abnormal data is superimposed), 2300: table, 2301: column (sample ID), 2302: column (test item), 2303: column (reference data ID), 2304: column (approximate equation/evaluation parameter value, test value), 2305: column (removal determination result), 2306: column (deviation determination result), 2307: column (reason of removal), 2308: column (reason of deviation), 2310: table, 2311: column (reference data ID), 2312: column (sample ID), 2320: table, 2321: column (reference data ID), 2322: column (type of regression function), 2323: column (regression function parameter), 2324: column (standard range)

The invention claimed is:

1. An automatic analysis device that mixes a sample and a reagent to measure temporal change of a mixed solution, the automatic analysis device comprising:
    a measurement point data acquisition unit that acquires a plurality of measurement point data from a reaction process of the sample and the reagent;
    a first storage unit that accumulates test values and parameters of approximate equations for approximating the plurality of measurement point data;
    a data processing unit that creates a distribution map of reference data corresponding to the parameters or the test values based on predetermined numbers of the parameters or the test values accumulated in the first storage unit;
    a second storage unit that stores a threshold for removal determination;
    an output unit that presents, on a display screen, removal data candidates included in the distribution map of the reference data based on the threshold; and
    a third storage unit that stores attached information of the reference data, the information including a determination result indicating whether data is to be removed from the distribution map of the reference data.

2. The automatic analysis device according to claim 1, wherein
    the output unit displays, on the display screen, a reaction process curve including a plurality of measurement point data corresponding to reference data designated and input on the distribution map.

3. The automatic analysis device according to claim 1, wherein
    when the determination result indicates removal, the third storage unit stores information related to a reason for removing the reference data from the distribution map.

4. The automatic analysis device according to claim 1, wherein
    the output unit presents a relationship between the threshold and the removal data candidates on the distribution map of the reference data.

5. The automatic analysis device according to claim 1, further comprising:
    a deviation determination unit that determines whether newly acquired test data is deviated from the distribution map of the reference data; and
    a fourth storage unit that stores attached information of the reference data, the information including a determination result indicating whether data is deviated from the distribution map of the reference data, wherein
    the output unit presents the determination result of the deviation determination unit on the distribution map of the reference data.

6. The automatic analysis device according to claim 5, wherein
    when the determination result indicates deviation, the fourth storage unit stores information related to a reason that the reference data is deviated from the distribution map.

7. The automatic analysis device according to claim 5, further comprising:
    a second data processing unit that calculates a second regression function indicating a relationship between the parameters and the test values corresponding to the reference data included in the distribution map; and
    a third data processing unit that calculates an ideal reaction process curve for arbitrary test data based on the second regression function, wherein
    the output unit superimposes, on the display screen, a reaction process curve corresponding to the test data determined to be deviated by the deviation determination unit and the ideal reaction process.

8. The automatic analysis device according to claim 5, further comprising:
    a fourth data processing unit that standardizes a cluster of reference data included in the distribution map of the reference data;
    a fifth data processing unit that standardizes the data removed from the distribution map of the reference data; and
    a sixth data processing unit that creates a standardized distribution map by merging a distribution of normal data created by the fourth data processing unit and a distribution of abnormal data created by the fifth data processing unit, in a way that allows identifying the distributions, wherein
    the output unit displays the standardized distribution map on the display screen.

9. The automatic analysis device according to claim 5, further comprising
    a fourth data processing unit that standardizes a cluster of reference data included in the distribution map of the reference data;
    a seventh data processing unit that standardizes the test data determined to be deviated by the deviation determination unit among the newly acquired test data; and
    an eighth data processing unit that creates a standardized distribution map by merging a distribution of normal data created by the fourth data processing unit and a distribution of abnormal data created by the seventh data processing unit, in a way that allows identifying the distributions, wherein
    the output unit displays the standardized distribution map on the display screen.

10. The automatic analysis device according to claim 9, further comprising
a ninth data processing unit that applies data processing opposite the standardization to the standardized distribution map to create a distribution map that can identify the normal data and the abnormal data, wherein
the output unit superimposes the newly acquired test data on the distribution map created by the ninth data processing unit.

11. An automatic analysis program causing a computer mounted on an automatic analysis device, which mixes a sample and a reagent to measure temporal change of a mixed solution, to execute:
a process of acquiring a plurality of measurement point data from a reaction process of the sample and the reagent;
a process of accumulating, in a first storage unit, test values parameters of approximate equations for approximating the plurality of measurement point data;
a process of creating a distribution map of reference data corresponding to the parameters or the test values based on predetermined numbers of the parameters or the test values accumulated in the first storage unit;
a process of presenting, on a display screen, removal data candidates included in the distribution map of the reference data based on a threshold for removal determination; and
a processing of storing, in a second storage unit, attached information of the reference data, the information including a determination result indicating whether data is to be removed from the distribution map of the reference data.

* * * * *